US012648936B2

(12) United States Patent
Bonazzi et al.

(10) Patent No.: US 12,648,936 B2
(45) Date of Patent: Jun. 9, 2026

(54) ISOTHIAZOLIDINE 1,1-DIOXIDE AND 1,4-BUTAN SULTONE CONTAINING RAPAMYCIN DERIVATIVES AND USES THEREOF

(71) Applicant: NOVARTIS AG, Basel (CH)

(72) Inventors: Simone Bonazzi, Cambridge, MA (US); Michael Connolly, Salem, MA (US); David Jonathan Glass, Cortland Manor, NY (US); Andrew W. Patterson, Somerville, MA (US); Tea Shavlakadze, Hawthorne, NY (US)

(73) Assignee: NOVARTIS AG, Basel (CH)

( * ) Notice: Subject to any disclaimer, the term of this patent is extended or adjusted under 35 U.S.C. 154(b) by 1018 days.

(21) Appl. No.: 17/442,733

(22) PCT Filed: Mar. 25, 2020

(86) PCT No.: PCT/IB2020/052825

§ 371 (c)(1),
(2) Date: Sep. 24, 2021

(87) PCT Pub. No.: WO2020/194209

PCT Pub. Date: Oct. 1, 2020

(65) Prior Publication Data

US 2022/0202787 A1 Jun. 30, 2022

Related U.S. Application Data

(60) Provisional application No. 62/824,190, filed on Mar. 26, 2019.

(51) Int. Cl.
*A61K 31/439* (2006.01)
*A61K 45/06* (2006.01)
*C07D 498/18* (2006.01)

(52) U.S. Cl.
CPC ............ *A61K 31/439* (2013.01); *A61K 45/06* (2013.01); *C07D 498/18* (2013.01)

(58) Field of Classification Search
CPC ..... A61K 45/06; A61K 31/439; C07D 498/18
See application file for complete search history.

(56) References Cited

U.S. PATENT DOCUMENTS

| | | | |
|---|---|---|---|
| 3,929,992 | A | 12/1975 | Sehgal et al. |
| 4,316,885 | A | 2/1982 | Rakhit |
| 4,650,803 | A | 3/1987 | Stella et al. |
| 5,120,842 | A | 6/1992 | Failli et al. |
| 5,151,413 | A | 9/1992 | Caufield et al. |
| 5,258,389 | A | 11/1993 | Goulet et al. |
| 5,362,718 | A | 11/1994 | Skotnicki et al. |
| 5,527,907 | A | 6/1996 | Or et al. |
| 5,665,772 | A | 9/1997 | Cottens et al. |
| 5,985,890 | A | 11/1999 | Cottens et al. |
| 6,384,046 | B1 | 5/2002 | Schuler et al. |
| 8,906,374 | B2 | 12/2014 | Kim et al. |
| 9,358,236 | B2 | 6/2016 | Murphy et al. |
| 9,427,463 | B2 | 8/2016 | Kim et al. |
| 9,669,032 | B2 | 6/2017 | Liu et al. |
| 9,683,048 | B2 | 6/2017 | Freeman et al. |
| 10,800,793 | B2 | 10/2020 | Bonazzi et al. |
| 12,091,424 | B2 | 9/2024 | Bonazzi et al. |
| 12,281,125 | B2 | 4/2025 | Bonazzi et al. |

(Continued)

FOREIGN PATENT DOCUMENTS

| | | | |
|---|---|---|---|
| CN | 1187821 | A | 7/1998 |
| CN | 1371378 | A | 9/2002 |

(Continued)

OTHER PUBLICATIONS

Combe (Best Practice & Research Clinical Rheumatology vol. 21, No. 1, pp. 27-42, 2007) (Year: 2007).*
Eynott (Immunology 2003, 109, 461-467) (Year: 2003).*
Festuccia (Immunobiology 222 (2017) 261-271) (Year: 2017).*
Kasai (Genes and Environment (2016) 38:19) (Year: 2016).*
Bae-Jump et al., (2010). "Rapamycin inhibits cell proliferation in type I and type II endometrial carcinomas: a search for biomarkers of sensitivity to treatment," Gynecol Oncol, 119(3):579-585, 18 pages.
Baker et al., (2016). "Naturally occurring p16(Ink4a)-positive cells shorten healthy lifespan", Nature, 530(7589):184-203, 30 pages.

(Continued)

*Primary Examiner* — Kortney L. Klinkel
*Assistant Examiner* — Richard Grant Peckham
(74) *Attorney, Agent, or Firm* — MORRISON & FOERSTER LLP

(57) ABSTRACT

Described herein are compounds of Formula (I) that are inhibitors of mTORC1, pharmaceutical compositions including such compounds, and methods of using such compounds and compositions.

(I)

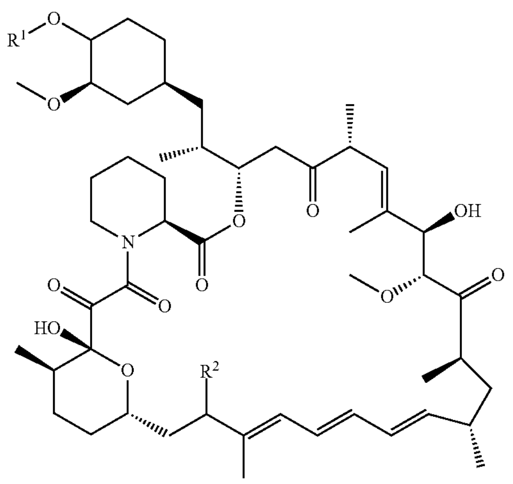

24 Claims, 2 Drawing Sheets

Specification includes a Sequence Listing.

(56) References Cited

U.S. PATENT DOCUMENTS

| | | | |
|---|---|---|---|
| 2019/0031683 A1 | 1/2019 | Saiah et al. |
| 2020/0392159 A1 | 12/2020 | Bonazzi et al. |
| 2021/0220339 A1 | 7/2021 | Saiah et al. |
| 2022/0064185 A1 | 3/2022 | Bonazzi et al. |
| 2022/0242878 A1 | 8/2022 | Bonazzi et al. |
| 2024/0360153 A1 | 10/2024 | Glass et al. |
| 2025/0223297 A1 | 7/2025 | Bonazzi et al. |

FOREIGN PATENT DOCUMENTS

| | | | |
|---|---|---|---|
| CN | 101389337 | A | 3/2009 |
| CN | 104202984 | A | 12/2014 |
| EA | 011488 | B1 | 4/2009 |
| EP | 1212331 | B1 | 4/2004 |
| JP | H07509246 | A | 10/1995 |
| JP | 2000510815 | A | 8/2000 |
| JP | 2002508971 | A | 3/2002 |
| JP | 2002514165 | A | 5/2002 |
| JP | 2002514893 | A | 5/2002 |
| JP | 2009527520 | A | 7/2009 |
| KR | 19990022780 | A | 3/1999 |
| RU | 2126409 | C2 | 2/1999 |
| RU | 2325906 | C2 | 6/2008 |
| WO | WO-1994002136 | A1 | 2/1994 |
| WO | WO-1996041807 | A1 | 12/1996 |
| WO | WO-1996041865 | A1 | 12/1996 |
| WO | WO-1997035575 | A1 | 10/1997 |
| WO | WO-1999036553 | A2 | 7/1999 |
| WO | WO-2001014387 | A1 | 3/2001 |
| WO | WO-2008022256 | A2 | 2/2006 |
| WO | WO-2007085400 | A1 | 8/2007 |
| WO | WO-2007096174 | A1 | 8/2007 |
| WO | WO-2012103959 | A1 | 8/2012 |
| WO | WO-2016207205 | A1 | 12/2016 |
| WO | WO-2017044720 | A1 | 3/2017 |
| WO | WO-2018204416 | A1 | 11/2018 |
| WO | WO-2019064182 | A1 | 4/2019 |

OTHER PUBLICATIONS

Baraz et al., (2014). "mTOR inhibition by everolimus in childhood acute lymphoblastic leukemia induces caspase-independent cell death," PLoS One, 9(7):e102494.
Battelli et al., (2011). "mTOR inhibitors in renal cell carcinoma," Therapy, 8(4):359-367, 14 pages.
Bayle et al., (2006). "Rapamycin Analogs with Differential Binding Specificity Permit Orthogonal Control of Protein Activity," Chemistry And Biology, 13(1):99-107.
Buss et al., (2009). "Beneficial Effects of Mammalian Target of Rapamycin Inhibition on Left Ventricular Remodeling After Myocardial Infarction", Journal of American College of Cardiology, 54(25):2435-2446.
Buss et al., (2010). "Augmentation of autophagy by mTOR-inhibition in myocardial infarction: When size matters", Autophagy, 6(2):304-306.
Cai et al., (2013). "mTOR inhibitor RAD001 (everolimus) induces apoptotic, not autophagic cell death, in human nasopharyngeal carcinoma cells," Int J Mol Med, 31(4):904-912.
Cassano et al., (2019). "Early intrathecal infusion of everolimus restores cognitive function and mood in a murine model of Alzheimer's disease," Exp Neurol, 311:88-105.
Chang et al., (2017). "Regression of Neonatal Cardiac Rhabdomyoma in Two Months Through Low-Dose Everolimus Therapy: A Report of Three Cases," Pediatr Cardiol, 38(7):1478-1484.
Chinnery (2015). "Mitochondrial disease in adults: what's old and what's new", EMBO Molecular Medicine, 7(2):1503-1512.
Ciołczyk-Wierzbicka et al., (2020). "mTOR inhibitor everolimus reduces invasiveness of melanoma cells," Hum Cell, 33(1):88-97.
Cuppens et al., (2017). "Potential Targets Analysis Reveals Dual PI3K/mTOR Pathway Inhibition as a Promising Therapeutic Strategy for Uterine Leiomyosarcomas-an ENITEC Group Initiative," Clin Cancer Res, 23(5): 1274-1285.
Doi et al., (2010). "Multicenter phase II study of everolimus in patients with previously treated metastatic gastric cancer," J Clin Oncol, 28(11):1904-1910.
Ehninger et al., (2008). "Reversal of learning deficits in a Tsc2+/− mouse model of tuberous sclerosis", Nature Medicine, 14(8):843-848, 15 pages.
Elnaggar et al., (2016). "Addition of Everolimus Post VEGFR Inhibition Treatment Failure in Advanced Sarcoma Patients Who Previously Benefited from VEGFR Inhibition: A Case Series," PLoS One, 11(6):e0156985, 7 pages.
Fanoudi et al., (2018). "Everolimus, a mammalian target of rapamycin inhibitor, ameliorated streptozotocin-induced learning and memory deficits via neurochemical alterations in male rats," EXCLI J, 17:999-1017.
Ghidini et al., (2017). "Clinical development of mTor inhibitors for renal cancer," Expert Opin. Investig. Drugs, 26:1229-1237.
Guenther et al., (2009). "Phase I/II Study with Single Agent Everolimus (RAD001) in Patients with Relapsed or Refractory Multiple myeloma," Blood, 114(22):3850, 2 pages.
Gulhati et al., (2012). "Sorafenib enhances the therapeutic efficacy of rapamycin in colorectal cancers harboring oncogenic KRAS and PIK3CA," Carcinogenesis, 33(9):1782-1790.
Günther et al., (2015). "Activity of everolimus (RAD001) in relapsed and/or refractory multiple myeloma: a phase I study," Haematologica, 100(4):541-547.
Guo et al., (2016). "Everolimus exhibits anti-tumorigenic activity in obesity-induced ovarian cancer," Oncotarget, 7(15):20338-20356.
Harrison et al., (2009). "Rapamycin fed late in life extends lifespan in genetically heterogeneous mice", Nature, 460(7253):392-396, 11 pages.
Holmes (2007). "Tuberous Sclerosis Complex and Epilepsy: Recent Developments and Future Challenges," Epilepsia, 48(4):617-630.
Hujber et al., (2017). "Rapamycin (mTORC1 inhibitor) reduces the production of lactate and 2-hydroxyglutarate oncometabolites in IDH1 mutant fibrosarcoma cells," J Exp Clin Cancer Res, 36(1):74, 12 pages.
International Search Report and Written Opinion received for International Patent Application No. PCT/IB2018/057422 mailed on Jan. 3, 2019, 10 pages.
International Search Report and Written Opinion received for International Patent Application No. PCT/IB2019/060957 mailed on Mar. 19, 2020, 10 pages.
International Search Report and Written Opinion received for International Patent Application No. PCT/IB2020/052825 mailed on May 28, 2020, 11 pages.
Johnston et al., (2018). "Phase 2 study of everolimus for relapsed or refractory classical Hodgkin lymphoma," Exp Hematol Oncol., 7:12, 10 pages.
Kabat et al., (2012). "Focal cortical dysplasia—review," Pol. J Radial., 77(2):35-43.
Kaeberlein et al., (2005). "Regulation of Yeast Replicative Life Span by TOR and Sch9 in Response to Nutrients," Science, 310(5751):1193-1196.
Kaeberlein et al., (2019). "Rapamycin and Alzheimer's disease: Time for a clinical trial?" Sci Transl Med, 11(476):aar4289, 10 pages.
Kang et al., (2021). "Impact of everolimus on survival after liver transplantation for hepatocellular carcinoma," Clin Mol Hepatol, 27(4):589-602.
Kapahi et al., (2004). "Regulation of Lifespan in *Drosophila* by Modulation of Genes in the TOR Signaling Pathway," Current Biology, 14:885-890, 8 pages.
Khan et al., {2017). "mTORC1 Regulates Mitochondrial Integrated Stress Response and Mitochondrial Myopathy Progression," Cell Metabolism, 26:419-428, 16 pages.
Koopman et al., {2016). "Mitochondrial disorders in children: toward development of small-molecule treatment strategies," EMBO Molecular Medicine, 8(4):311-327.
Kummerer (2010). "Pharmaceuticals in the environment," Annual Review Of Environment And Resources, 35:57-75.

(56) References Cited

OTHER PUBLICATIONS

Kwitkowski et al., (2010). "FDA Approval Summary: Temsirolimus as Treatment for Advanced Renal Cell Carcinoma," The Oncologist, 15(4):428-435.
Laplante et al., (2012). "mTOR Signaling in Growth Control and Disease," Cell, 149(2):274-293.
Lee et al., (2007). "mTOR Pathway as a Target in Tissue Hypertrophy," Ann. Rev. Pharmacol. Toxicol., 47:7.1-7.25.
Lin et al., (2017). "Rapamycin rescues vascular, metabolic and learning deficits in apolipoprotein E4 transgenic mice with pre-symptomatic Alzheimer's disease," J Cereb Blood Flow Metab, 37(1):217-226.
Ljungberg et al., (2009). "Rapamycin suppresses seizures and neuronal hypertrophy in a mouse model of cortical dysplasia," Dis Model Mech., 2(7-8):389-398.
Luengo et al., (1995). "Structure-Activity Studies Of Rapamycin Analogs: Evidence That The C-7 Methoxy Group Is Part Of The Effector Domain And Positioned At The Fkbp12-Frap Interface," Chemistry And Biology, 2(7):471-481.
Mabuchi et al., (2009). "mTOR is a promising therapeutic target both in cisplatin-sensitive and cisplatin-resistant clear cell carcinoma of the ovary," Clin Cancer Res, 15(17):5404-5413, 21 pages.
Mannick et al., (2014). "mTOR inhibition improves immune function in the elderly," Science Translational Medicine, 6(268), 12 pages.
Manning et al., (2002). "Identification of the Tuberous Sclerosis Complex-2 Tumor Suppressor Gene Product Tuberin as a Target of the Phosphoinositide 3-Kinase/Akt Pathway," Molecular Cell, 10:151-162.
Martin et al., (2012). "Effectiveness and molecular interactions of the clinically active mTORC1 inhibitor everolimus in combination with tamoxifen or letrozole in vitro and in vivo," Breast Cancer Res, 14(5):R132, 15 pages.
Marz et al., (2013). "Large FK506-Binding Proteins Shape the Pharmacology of Rapamycin," Molecular and Cellular Biology, 33(7):1357-1367.
McAlpine et al., (1991). "Revised NMR assignments for rapamycin," J. Antibiot. (Tokyo) 44:688-690.
Meikle et al., (2008). "Response of a Neuronal Model of Tuberous Sclerosis to Mammalian Target of Rapamycin (mTOR) Inhibitors: Effects on mTORC1 and Akt Signaling Lead to Improved Survival and Function," The Journal of Neuroscience, 28(21):5422-5432.
Miklja et al., (2020). "Everolimus improves the efficacy of dasatinib in PDGFRα-driven glioma," J Clin Invest, 130(10):5313-5325.
Miller et al., (2014). "Rapamycin-mediated lifespan increase in mice is dose and sex dependent and metabolically distinct from dietary restriction," Aging Cell, 13(3): 468-477.
Milowsky et al., (2013). "Phase II study of everolimus in metastatic urothelial cancer," BJU Int, 112(4):462-470.
Molinolo et al., (2012). "mTOR as a molecular target in HPV-associated oral and cervical squamous carcinomas," Clin Cancer Res, 18(9):2558-2568, 19 pages.
Moriya et al., (2014). "Antitumor effect and antiangiogenic potential of the mTOR inhibitor temsirolimus against malignant pleural mesothelioma," Oncol Rep, 31(3):1109-1115.
Ozcelik et al., (2013). "Rapamycin attenuates the progression of tau pathology in P301S tau transgenic mice," PLoS One, 8(5):e62459, 7 pages.
Pleniceanu et al., (2018). "mTORC1 Inhibition Is an Effective Treatment for Sporadic Renal Angiomyolipoma," Kidney International Reports, 3:155-159.
Poore et al., (2019). "Inhibition of mTORC1 in pediatric low-grade glioma depletes glutathione and therapeutically synergizes with carboplatin," Neuro Oncol, 21(2):252-263.
Ray-Coquard et al., (2013). "Everolimus as second- or third-line treatment of advanced endometrial cancer: ENDORAD, a phase II trial of GINECO," Br J Cancer, 108(9):1771-1777.
Royce et al., (2015). "Everolimus in the Treatment of Metastatic Breast Cancer," Breast Cancer: Basic and Clinical Research, 9:73-79.
Selman et al., (2009). "Ribosomal Protein S6 Kinase 1 Signaling Regulates Mammalian Life Span," Science, 326(5949):140-144.
Shavlakadze et al., (2018). "Short-term Low-Dose mTORC1 Inhibition in Aged Rats Counter-Regulates Age-Related Gene Changes and Blocks Age-Related Kidney Pathology," J Gerontol A Biol Sci Med Sci., 73(7):845-852.
Silic-Benussi et al., (2022). "mTOR inhibition downregulates glucose-6-phosphate dehydrogenase and induces ROS-dependent death in T-cell acute lymphoblastic leukemia cells," Redox Biol, 51:102268, 14 pages.
Siman et al., (2015). "The mTOR Inhibitor Rapamycin Mitigates Perforant Pathway Neurodegeneration and Synapse Loss in a Mouse Model of Early-Stage Alzheimer-Type Tauopathy," PLoS One, 10(11):e0142340, 21 pages.
Spilman et al., (2011). "Inhibition of mTOR by rapamycin abolishes cognitive deficits and reduces amyloid-beta levels in a mouse model of Alzheimer's disease," PLoS One, 5(4):e9979, 8 pages.
Sun et al., (2012). "Chemopreventive and chemotherapeutic actions of mTOR inhibitor in genetically-defined head and neck squamous cell carcinoma mouse model," Clin Cancer Res, 18(19):5304-5313, 18 pages.
Vellai et al., (2003). "Influence of TOR kinase on lifespan in C. elegans," Nature, 426:620.
Vera Aguilera et al., (2018). "Phase II Study of Everolimus in Metastatic Malignant Melanoma (NCCTG-N0377, Alliance)," Oncologist, 23(8):887-e94.
Villamil et al., {2014). "Fibrosis progression in maintenance liver transplant patients with hepatitis C recurrence: a randomised study of everolimus vs. calcineurin inhibitors," Liver, 34(10):1513-1521, 9 pages.
Wolpin et al., (2013). "Multicenter phase II study of tivozanib (AV-951) and everolimus (RAD001) for patients with refractory, metastatic colorectal cancer," Oncologist, 18:377-378.
Wong (2013). "Mammalian target of rapamycin (mTOR) activation in focal cortical dysplasia and related focal cortical malformations," Experimental Neurology, 244:22-26, 11 pages.
Yao et al., (2011). "Everolimus for advanced pancreatic neuroendocrine tumors," N Engl J Med, 364(6):514-523.
Yao et al., (2016). "Everolimus for the treatment of advanced, nonfunctional neuroendocrine tumours of the lung or gastrointestinal tract (RADIANT-4): a randomised, placebo-controlled, phase 3 study," Lancet, 387(10022):968-977, 20 pages.
Yi et al., (2020). "Safety and efficacy of sirolimus combined with endocrine therapy in patients with advanced hormone receptor-positive breast cancer and the exploration of biomarkers," Breast, 52:17-22.
Yoo et al., (2013). "Multicenter phase II study of everolimus in patients with metastatic or recurrent bone and soft-tissue sarcomas after failure of anthracycline and ifosfamide," Invest New Drugs, 31(6):1602-1608.
Young et al., (2016). "Human mitochondrial DNA replication machinery and disease," Current Opinion in Genetics & Development, 38:52-62, 20 pages.
Yu et al., (2021). "Efficient Everolimus Treatment for Metastatic Castration Resistant Prostate Cancer with AKT1 Mutation: A Case Report," Onco Targets Ther, 14:5423-5428.
Zeng et al., (2008). "Rapamycin Prevents Epilepsy in a Mouse Model of Tuberous Sclerosis Complex," Ann. Neuorol., 63(4):444-453, 16 pages.
Zeng et al., {2009). "The Mammalian Target of Rapamycin Signaling Pathway Mediates Epileptogenesis in a Model of Temporal Lobe Epilepsy," The Journal of Neuroscience, 29(21):6964-6972.
Zhou et al., {2009). "Pharmacological Inhibition of mTORC1 Suppresses Anatomical, Cellular, and Behavioral Abnormalities in Neural-Specific Pten Knock-Out Mice," The Journal of Neuroscience, 29(6):1773-1783.
Zhu et al., (2011). "Phase 1/2 study of everolimus in advanced hepatocellular carcinoma," Cancer, 117(22):5094-5102.
Zureick et al., (2019). "Successful treatment of a TSC2-mutant glioblastoma with everolimus," BMJ Case Rep, 12(5):e227734, 4 pages.

(56) References Cited

OTHER PUBLICATIONS

Bastin et al., (2000). "Salt Selection and Optimisation Procedures for Pharmaceutical New Chemical Entities," Organic Process Research & Development, 4(5):427-435.
Belikov, (2007). "Chapter 2.6: Relationship between the chemical structure, properties of substances and their effect on the body," in Pharmaceutical Chemistry Med Press Inform, pp. 27-29, 9 pages. English translation.
Berge et al., (1977). "Pharmaceutical salt," J. Pharmaceutical Sciences, 66:1-19.
Durnov et al., (2002). "Pediatric Oncology," 2nd edition, Moscow: "Meditsina" publishing house, p. 139, 5 pages. English translation.
Emsley et al., (2010). "Features and development of Coot," Acta Crystallographica Section D: Biological Crystallography, D66:486-501.
Inoki et al., (2005). "Dysregulation of the TSC-mTOR pathway in human disease," Nature Genetics, 37(7):19-24, 13 pages.
Kabsch, (2010). "XDS," Acta Cryst. D, 66:125-132.
Mashkovsky, (2001). "Medicines", 14th edition, vol. 1, Moscow, p. 11, 3 pages. English translation.
Murshudov et al., (2011). "REFMAC5 for the refinement of macromolecular crystal structures," Acta Crystallographica Section D: Biological Crystallography, 67(Pt 4):355-367.
Pinto-Leite et al., (2012). "Everolimus enhances gemcitabine-induced cytotoxicity in bladder-cancer cell lines," J Toxicol Environ Health A, 75(13-15):788-99. Abstract Only.
Collaborative Computational Project, No. 4 (1994). "The CCP4 suite: programs for protein crystallography," Acta Crystallogr D Biol Crystallogr, 50(Pt 5):760-3.
D'Arcy et al., (2007). "An automated microseed matrix-screening method for protein crystallization," Acta Crystallogr D Biol Crystallogr, 63(Pt 4):550-554. Abstract Only.
Dickman et al., (2000). "Antifungal rapamycin analogues with reduced immunosuppressive activity," Bioorganic & Medicinal Chemistry Letters, 10(13):1405-1408.
Hughes et al., (1992). "The Isolation, synthesis and characterization of an Isomeric Form of Rapamycin," Tetrahedron Letters, 33(33):4739-4742. Abstract Only.
Jiang et al., (2014). "Temsirolimus promotes autophagic clearance of amyloid-β and provides protective effects in cellular and animal models of Alzheimer's disease," Pharmacol Res, 81:54-63.
Leslie (2015). "A Putative Antiaging Drug Takes a Step From Mice to Men," Science, 342(6160):789.
Luengo et al., (1994). "Manipulation Of The Rapamycin Effector Domain. Selective Nucleophilic Substitution Of The C7 Methoxy Group," Journal Of Organic Chemistry, 59(22): 6512-6513.
Merli et al., (2015). "Everolimus in diffuse large B-cell lymphomas," Future Oncol, 11(3):373-83.
Mlerke et al., (1991). "Conformational Analysis of the cis-and trans-Isomers of FK506 by NMR and Molecular Dynamics," Helvetica Chimica Acta, 74(5):1027-1045. Abstract Only.
Van Duyne et al., (1991). "Atomic Structure of the Rapamycin Human Immunophilin FKBP-12 Complex," J. Am. Chem. Soc., 113(19):7433-7434. Abstract Only.
Nakagawa et al., (2013). "New immunosuppressive drug: mTOR inhibitor and thymoglobulin," Journal of the Japanese Society of Nephrology, 55(2):112-118. English translation.
Extended European Search Report and Written Opinion received for European Patent Application No. 24150040.4 mailed on Jun. 11, 2024, 9 pages.
International Preliminary Report on Patentability received for International Patent Application No. PCT/US2024/030861 mailed on Nov. 13, 2025, 8 pages.
International Search Report and Written Opinion received for International Patent Application No. PCT/US2024/030861 mailed on Sep. 9, 2024, 12 pages.
Invitation to Pay Additional Fees received for International Patent Application No. PCT/US2025/049852 mailed on Dec. 8, 2025, 3 pages.
Invitation to Pay Additional Fees received for International Patent Application No. PCT/US2024/030861 mailed on Jul. 8, 2024, 2 pages.
Nakajima et al., (1992). "MPM (4-methoxybenzyl) protection of hydroxy functions under mild acidic conditions," Tetrahedron Letters, 29(33):4139-4142.
Zhou et al., (2011). "Updates of mTOR inhibitors, Anti-Cancer Agents in Medicinal Chemistry," Anticancer Agents Med Chem, 10(7):571-81, 23 pages.

* cited by examiner

ISOTHIAZOLIDINE 1,1-DIOXIDE AND 1,4-BUTAN SULTONE CONTAINING RAPAMYCIN DERIVATIVES AND USES THEREOF

CLAIM OF PRIORITY

This application is an U.S. National Phase filing of International Application Serial No. PCT/IB2020/052825 filed 25 Mar. 2020, which claims priority from U.S. Provisional Application Ser. No. 62/824,190 filed 26 Mar. 2019, respectively, each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Aug. 11, 2021, is named PAT058487_SL.txt and is 785 bytes in size.

FIELD

This disclosure relates to C16-rapamycin derivatives that are inhibitors of mTORC1.

BACKGROUND

In mammalian cells, the target of rapamycin (mTOR) kinase exists in two distinct multiprotein complexes, described as the mTORC1 complex and the mTORC2 complex, both of which sense the availability of nutrients and energy, and integrate inputs from growth factors and stress signaling. mTORC1 integrates signals from growth factors and nutrients and controls cell growth and metabolism (Laplante M. et al. Cell. (2012) 149(2):274-93). mTORC1 is a key regulator of protein translation and autophagy. mTORC1 is sensitive to allosteric mTOR inhibitors such as rapamycin and rapamycin analogs (so called 'rapalogs'). Rapamycin and previously-produced rapalogs' mode of action involves the formation of an intracellular complex with the FK506 binding proteins, such as FKBP12, FKBP12.6, FKBP13, FKBP25, FKBP51, or FKBP52 (these FKBPs will be referenced here as "FKBP" or "FKBPs"), followed by the binding of the FKBP-rapalog complex to the FRB (FK506-rapamycin binding) domain of mTOR. März A. M. et al. Mol Cell Biol. (2013) 33(7):1357-1367. Such interaction of the FKBP-rapalog complex with mTORC1 results in allosteric inhibition of mTORC1. Rapamycin and rapalogs, such as RAD001 (everolimus; Afinitor®), have gained clinical relevance by inhibiting the activity of mTORC1, which is associated with both benign and malignant proliferation disorders. Royce M. E. et al. Breast Cancer (Auckl). (2015) 9:73-79; Pleniceanu O. et al. Kidney Int Rep. (2018) 3(1):155-159, and a variety of other indications.

Rapamycin is a known macrolide antibiotic produced by *Streptomyces hygoscopius*, see e.g. McAlpine, J. B., et al., J. Antibiotics (1991) 44:688; Schreiber, S. L.; et al., J. Am. Chem. Soc. (1991) 113:7433; U.S. Pat. No. 3,929,992. The following numbering convention for rapamycin and its derivatives used in this document is shown below:

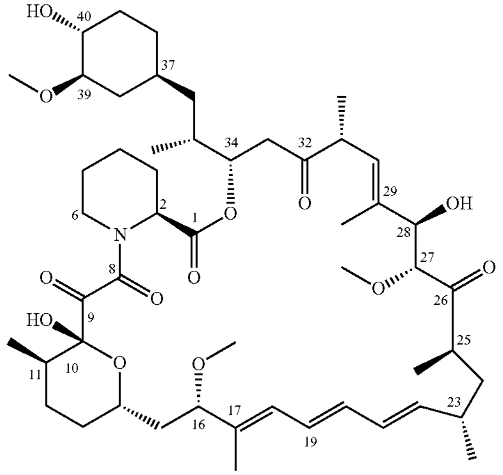

Rapamycin is a potent immunosuppressant and has also been shown to have antitumor and antifungal activity. It has been shown to be useful in preventing or treating systemic lupus erythematosus, pulmonary inflammation, insulin-dependent diabetes mellitus, skin disorders such as psoriasis, smooth muscle cell proliferation and intimal thickening following vascular injury, adult T-cell leukemia/lymphoma, malignant carcinomas, cardiac inflammatory disease, anemia and increased neurite outgrowth. Its utility as a pharmaceutical, however, is restricted by its very low and variable bioavailability. Moreover, rapamycin is challenging to formulate, making it difficult to obtain stable galenic compositions.

In animal models, rapamycin and the rapalogs extend lifespan and/or delay the onset of age-related diseases. Aging, like other biological processes, is regulated by signaling pathways such as the TOR pathway (named "TOR" in this case, to include the yeast and *C elegans* systems) and, in mammals, the mTORC1 pathway. Modulation of TOR and mTORC1 signaling prolongs lifespan and delays the onset of age-related diseases in a wide array of organisms, from flies to mammals. For instance, inhibition of the TOR pathway by genetic mutation extended lifespan in yeast, *C elegans*, and drosophila, and inhibition of the mTORC1 pathway extended lifespan in mice (Kaeberlein et al., Science (2005) 310:1193-1196; Kapahi et al., Curr Biol (2004) 14:885-890; Selman et al., Science (2009) 326:140-144; Vellai et al., Nature (2003) 426:620; R. A. Miller et al. Aging Cell. (2014) 13(3): 468-477.) In addition, the mTORC1 inhibitor rapamycin extended the lifespan of mice even when given late in life (Harrison et al., Nature (2009) 460(7253):392-395). These data raise the possibility that drugs that target the mammalian TOR (mTOR) pathway will have therapeutic effects in aging and age-related diseases in humans. A report of a clinical trial using rapamycin in elderly men was described by M. Leslie in Science, 2013, 342. J. Mannick et al. describe in Sci Transl Med. (2014) 6(268): 268ra179 that mTORC1 inhibition improves the immune function in the elderly. However, investigators have been wary of using currently available mTORC1 inhibitors in human aging trials due to their side effects (including immunosuppression, cytopenias, stomatitis, GI distress and interstitial pneumonitis).

Pharmacological inhibition of the mTORC1 pathway, either before or immediately following neurological insults, can prevent pathological changes in animal brains and the development of spontaneous recurrent seizure in an acquired epilepsy model (Zeng et al., The mammalian target of rapamycin signaling pathway mediates epileptogenesis in a model of temporal lobe epilepsy; J. Neurosci., (2009) pp. 6964-6972). Rapamycin and rapalogs are therefore also considered to be of potential value in such indications.

Rapalogs have been shown to be efficacious at low doses in human beings in settings of liver and kidney fibrosis.

Mitochondrial myopathy (MM) is the most common manifestation of adult-onset mitochondrial disease and shows a multifaceted tissue-specific stress response: (1) transcriptional response, including metabolic cytokines FGF21 and GDF15; (2) remodeling of one-carbon metabolism; and (3) the mitochondrial unfolded protein response. In Cell Metabolism 26, 419-428, Aug. 1, 2017, it is described by Khan et al. that these processes are part of one integrated mitochondrial stress response (ISRmt), which is controlled by mTORC1 in skeletal muscle. A mtDNA replication defect activates mTORC1, which drives an integrated mitochondrial stress response through ATF4 activation, inducing de novo nucleotide and serine synthesis, the 1C-cycle, and FGF21 and GDF15 production. mTORC1 inhibition by rapamycin downregulated all components of the ISRmt (integrated mitochondrial stress response), improved all MM hallmarks, and reversed the progression of even late-stage MM, without inducing mitochondrial biogenesis. Rapamycin and rapalogs are therefore also considered to be of potential value in such indications.

Thus, there remains a need to provide new mTORC1 inhibitors that are improved drug candidates, exhibiting a balance of appropriate potency, stability, and bioavailability.

SUMMARY

The compounds of Formula (I) are mTORC1 inhibitors and are useful in the treatment of disorders, particularly age-related disorders, or diseases and disorders currently approved for treatment using rapamycin or any of the rapalogs. Replacement of the C16 methoxy group as described herein, provides compounds exhibiting a balance of appropriate potency, stability and bioavailability. The compounds of Formula (I) are effective in inhibiting mTORC1 by selectively binding to FKBP12 in settings where FKBP12 levels are sufficient to inhibit mTORC1.

In one aspect, the disclosure provides a compound of Formula (I) or a pharmaceutically acceptable salt thereof, wherein:

(I)

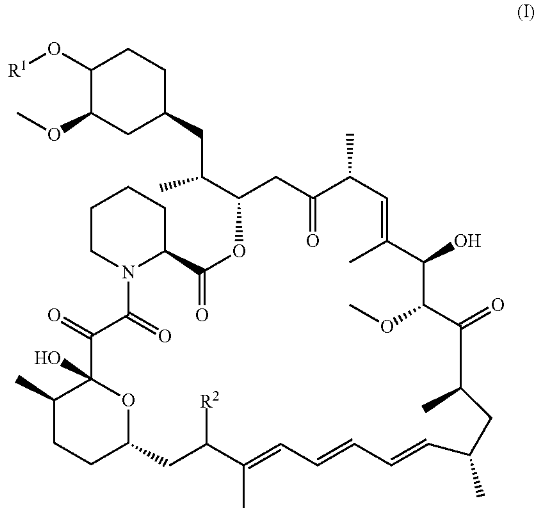

$R^1$ is selected from the group consisting of hydrogen, $C_{1-6}$ alkyl, hydroxyl$C_{1-6}$alkyl, and hetero$C_{1-6}$alkyl; and $R^2$ is

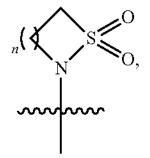

wherein n is 1, 2 or 3.

In an embodiment, the disclosure provides a pharmaceutical composition comprising a therapeutically effective amount of a compound of Formula (I) or a pharmaceutically acceptable salt thereof, and one or more pharmaceutically acceptable carriers.

In an embodiment, the disclosure provides a pharmaceutical combination comprising a therapeutically effective amount of a compound of Formula (I) or a pharmaceutically acceptable salt thereof, and one or more therapeutically active agents.

In another aspect, the disclosure provides a method for treating a disorder or a disease mediated by the mTOR pathway in a subject in need thereof, the method comprising administering to the subject a therapeutically effective amount of a compound of Formula (I) or a pharmaceutically acceptable salt thereof.

In another aspect, the disclosure provides a method for treating a disease or disorder in a subject, wherein the target tissue, organ, or cells associated with the pathology of the disease or disorder has FKBP12 levels sufficient to inhibit mTORC1, the method comprising administering to the subject in need thereof a therapeutically effective amount of a compound of Formula (I) or a pharmaceutically acceptable salt thereof.

In another aspect, the disclosure provides a method for treating a disease or disorder in a subject having, or a subject that has been determined to have, FKBP12 levels sufficient to inhibit mTORC1, the method comprising administering to the subject in need thereof a therapeutically effective amount of a compound of Formula (I) or a pharmaceutically acceptable salt thereof.

In another aspect, the disclosure provides a method for treating an age-related disease or disorder in a subject in need thereof, the method comprising administering to the subject a therapeutically effective amount of a compound of Formula (I) or a pharmaceutically acceptable salt thereof.

In an embodiment, the age-related disease or disorder is selected from sarcopenia, skin atrophy, cherry angiomas, seborrheic keratoses, brain atrophy (also referred to as dementia), atherosclerosis, arteriosclerosis, pulmonary emphysema, osteoporosis, osteoarthritis, high blood pressure, cataracts, macular degeneration, glaucoma, stroke, cerebrovascular disease (strokes), chronic kidney disease, diabetes-associated kidney disease, impaired hepatic function, liver fibrosis, autoimmune hepatitis, endometrial hyperplasia, metabolic dysfunction, renovascular disease, hearing loss, mobility disability (e.g., frailty), cognitive decline, tendon stiffness, heart dysfunction such as cardiac hypertrophy and/or systolic and/or diastolic dysfunction and/or hypertension and/or dilated cardiomyopathy, heart dysfunction which results in a decline in ejection fraction, immune senescence, Parkinson's disease, Alzheimer's disease, cancer, immune-senescence leading to cancer due to a decrease in immune-surveillance, infections due to an decline in immune-function, chronic obstructive pulmonary disease (COPD), obesity, loss of taste, loss of olfaction, arthritis, and type II diabetes (including complications stemming from diabetes, such as kidney failure, blindness and neuropathy).

In another aspect, the disclosure provides a method for treating a disease or disorder in a subject in need thereof, the method comprising administering to the subject a therapeutically effective amount of a compound of Formula (I) or a pharmaceutically acceptable salt thereof, wherein the disease or disorder is selected from:

Transplant vasculopathies;

Smooth muscle cell proliferation and migration leading to vessel intimal thickening, blood vessel obstruction, obstructive coronary atherosclerosis, restenosis;

Autoimmune diseases and inflammatory conditions;

Asthma;

Multi-drug resistance (MDR);

Fungal infections;

Inflammation;

Infection;

Age-related diseases;

Neurodegenerative diseases;

Proliferative disorders, e.g., cancer;

Seizures and seizure related disorders; and

Mitochondrial myopathy and mitochondrial stress.

In another aspect, the disclosure provides a method for treating cancer in a subject in need thereof, the method comprising administering to the subject a therapeutically effective amount of a compound of Formula (I) or a pharmaceutically acceptable salt thereof.

In an embodiment, the method further comprises a PD-1/PDL-1 inhibitor.

In an embodiment, the cancer is selected from renal cancer, renal cell carcinoma, colorectal cancer, uterine sarcoma, endometrial uterine cancer, endometrial cancer, breast cancer, ovarian cancer, cervical cancer, gastric cancer, fibrosarcoma, pancreatic cancer, liver cancer, melanoma, leukemia, multiple myeloma, nasopharyngeal cancer, prostate cancer, lung cancer, glioblastoma, astrocytoma, adenocarcinoma, bladder cancer, mesothelioma, head cancer, rhabdomyosarcoma, sarcoma, lymphoma, and neck cancer.

In an embodiment, the disorder is a liver disorder that includes the process of fibrosis and/or inflammation, e.g., liver fibrosis that occurs in end-stage liver disease; liver cirrhosis; liver failure due to toxicity; non-alcohol-associated hepatic steatosis or NASH; and alcohol-associated steatosis.

In an embodiment, the disorder is a kidney disorder that includes the process of fibrosis or inflammation in the kidney, e.g., kidney fibrosis, or glomerulosclerosis, which occurs as a result of acute kidney injury, leading to chronic kidney disease. In an embodiment, the kidney disorder is chronic kidney disease arising in settings of diabetic nephropathy. In an embodiment, the chronic kidney disease leads to kidney failure.

In an embodiment, the disorder is a heart dysfunction, e.g., myocardial infarction or cardiac hypertrophy. In an embodiment, the heart dysfunction is systolic and/or diastolic dysfunction. In an embodiment, the heart dysfunction is hypertension. In an embodiment, the heart dysfunction results in a decline in ejection fraction. In an embodiment, heart failure may have preserved ejection fraction. In an embodiment, the heart dysfunction results in dilated cardiomyopathy.

In an embodiment, the disorder is an immune-senescence leading to cancer due to a decrease in immune-surveillance.

In an embodiment, the disorder is cancer, including tumors which are treated by immunotherapy. In an embodiment, the subject has been previously treated by either rapamycin, RAD001, or another rapalog. In an embodiment, the cancer includes tumors where the mTOR pathway is shown to be activated, including settings where there is a mutation in the Tsc1 gene, or where the tumor microenvironment is appropriately treated by a rapalog.

The details of one or more embodiments of the disclosure are set forth herein. Other features, objects, and advantages of the disclosure will be apparent from the FIGURES, the Detailed Description, the Examples, and the Claims.

DETAILED DESCRIPTION

Definitions

Figure 1A:
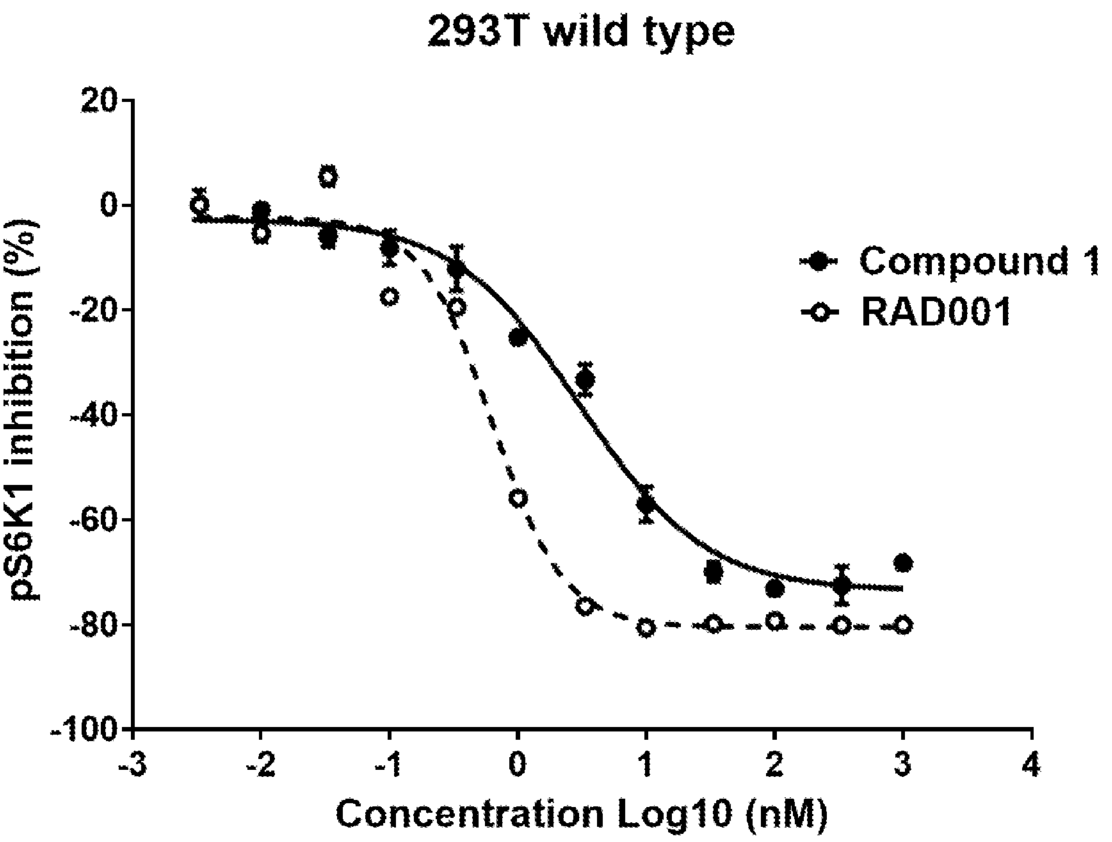
FIGS. 1A and 1B depict line graphs showing inhibition of S6K1(Thr389) in wild-type (FIG. 1A) and FKBP12 knockout (FIG. 1B) 293T cells, following treatment with Compound 1 (solid line) and RAD001 (dotted line). Cells were treated in triplicate. The Y axis represents percent inhibition of pS6K1(Thr389) relative to the level in cells treated with rapalog free media (media plus DMSO). The X axis represents concentrations for Compound 1 and RAD001.

Unless specified otherwise, the term "compounds of the disclosure" or "compound of the disclosure" refers to compounds of Formula (I), and exemplified compounds, and salts thereof, as well as all stereoisomers (including diastereoisomers and enantiomers), rotamers, tautomers and isotopically labeled compounds (including deuterium substitutions), as well as inherently formed moieties.

The term "a therapeutically effective amount" of a compound of the disclosure refers to an amount of the compound of the disclosure that will elicit the biological or medical response of a subject, for example, reduction or inhibition of an enzyme or a protein activity, or ameliorate symptoms, alleviate conditions, slow or delay disease progression, or prevent a disease, etc. In an embodiment, the term "a therapeutically effective amount" refers to the amount of the compound of the disclosure that, when administered to a subject, is effective to (1) at least partially alleviate, or ameliorate a condition, or a disorder or a disease (i) mediated by the mTOR pathway, or (ii) associated with mTOR activity, or (iii) characterized by activity (normal or abnormal) of mTOR; or (2) reduce or inhibit the activity of mTOR; or (3) reduce or inhibit the expression of mTOR. In an embodiment, the term "a therapeutically effective amount" refers to the amount of the compound of the disclosure that, when administered to a cell, or a tissue, or a non-cellular biological material, or a medium, is effective to at least partially reduce or inhibit the activity of mTOR; or at least partially reduce or inhibit the expression of mTOR.

As used herein, the term "subject" refers to primates (e.g., humans, male or female), dogs, cats, rabbits, guinea pigs, pigs, rats and mice. In certain embodiments, the subject is a primate. In yet other embodiments, the subject is a human.

The terms "administer," "administering," or "administration," as used herein refers to implanting, absorbing, ingesting, injecting, inhaling, or otherwise introducing an inventive compound, or a pharmaceutical composition thereof.

As used herein, the term "inhibit," "inhibition" or "inhibiting" refers to the reduction or suppression of a given condition, symptom, or disorder, or disease, or a significant decrease in the baseline activity of a biological activity or process.

As used herein, the term "treat", "treating," or "treatment" of any disease or disorder refers to alleviating, delaying the onset of, ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient. In an embodiment, "treatment," "treat," and "treating" require that signs or symptoms of the disease, disorder or condition have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

As used herein, the term "prevent", "preventing," or "prevention" of any disease or disorder refers to the prophylactic treatment of the disease or disorder; or delaying the onset or progression of the disease or disorder.

As used herein, "age-related disease or disorder" refers to any disease or disorder whose incidence in a population or severity in an individual correlates with the progression of age. More specifically, an age-related disease or disorder is a disease or disorder whose incidence is at least 1.5 fold higher among human individuals greater than 65 years of age relative to human individuals between the ages of 25-35. Examples of age-related disorders include, but are not limited to: sarcopenia, skin atrophy, cherry angiomas, seborrheic keratoses, brain atrophy (also referred to as dementia), atherosclerosis, arteriosclerosis, pulmonary emphysema, osteoporosis, osteoarthritis, high blood pressure, cataracts, macular degeneration, glaucoma, stroke, cerebrovascular disease (strokes), chronic kidney disease, diabetes-associated kidney disease, impaired hepatic function, liver fibrosis, autoimmune hepatitis, endometrial hyperplasia, metabolic dysfunction, renovascular disease, hearing loss, mobility disability (e.g., frailty), cognitive decline, tendon stiffness, heart dysfunction, such as cardiac hypertrophy, systolic or diastolic dysfunction, hypertension, dilated cardiomyopathy, heart dysfunction which results in a decline in ejection fraction, immune senescence, Parkinson's disease, Alzheimer's disease, cancer, immune-senescence leading to cancer due to a decrease in immune-surveillance, infections due to an decline in immune-function, chronic obstructive pulmonary disease (COPD), obesity, loss of taste, loss of olfaction, arthritis, and type II diabetes (including complications stemming from diabetes, such as kidney failure, blindness and neuropathy).

As used herein, a subject is "in need of" a treatment if such subject would benefit biologically, medically or in quality of life from such treatment.

As used herein, the term "a," "an," "the" and similar terms used in the context of the disclosure (especially in the context of the claims) are to be construed to cover both the singular and plural unless otherwise indicated herein or clearly contradicted by the context.

The term "alkyl" refers to a radical of a straight-chain or branched saturated hydrocarbon group having from 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl).

"Heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl").

"Hydroxy$C_{1-6}$alkyl" refers to an alkyl group substituted with one or more —OH groups. Examples of hydroxy-$C_{1-6}$alkyl groups include $HO—CH_2—$, $HO—CH_2CH_2—$, and $—CH_2—CH(OH)CH_3$.

"Hydroxy" or "hydroxyl" refers to —OH.

"Halo" or "halogen" refers to fluorine (fluoro, —F), chlorine (chloro, —Cl), bromine (bromo, —Br), or iodine (iodo, —I). In an embodiment, halogen refers to fluoro, chloro or bromo.

As used herein, the definition of each expression, e.g., alkyl, m, n, etc., when it occurs more than once in any structure, is intended to be independent of its definition elsewhere in the same structure.

Definitions of specific functional groups and chemical terms are described in more detail below. The chemical elements are identified in accordance with the Periodic Table of the Elements, CAS version, *Handbook of Chemistry and Physics*, $75^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's*

*Advanced Organic Chemistry,* 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis,* 3rd Edition, Cambridge University Press, Cambridge, 1987.

Certain compounds of the disclosure may exist in particular geometric or stereoisomeric forms. If, for instance, a particular enantiomer of a compound of the disclosure is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Unless otherwise stated, structures depicted herein are also meant to include geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the disclosed compounds are within the scope of the disclosure. Unless otherwise stated, all tautomeric forms of the compounds of the disclosure are within the scope of the disclosure. Additionally, unless otherwise stated, structures depicted herein are also meant to include compounds that differ only in the presence of one or more isotopically enriched atoms. For example, compounds having the disclosed structures including the replacement of hydrogen by deuterium or tritium, or the replacement of a carbon by a $^{13}C$- or $^{14}C$-enriched carbon are within the scope of this disclosure. Such compounds are useful, for example, as analytical tools, as probes in biological assays, or as therapeutic agents in accordance with the disclosure.

The "enantiomeric excess" or "% enantiomeric excess" of a composition can be calculated using the equation shown below. In the example shown below a composition contains 90% of one enantiomer, e.g., the S enantiomer, and 10% of the other enantiomer, i.e., the R enantiomer.

$$ee=(90-10)/100*100=80\%.$$

Thus, a composition containing 90% of one enantiomer and 10% of the other enantiomer is said to have an enantiomeric excess of 80%. The compounds or compositions described herein may contain an enantiomeric excess of at least 50%, 75%, 90%, 95%, or 99% of one form of the compound, e.g., the S-enantiomer. In other words, such compounds or compositions contain an enantiomeric excess of the S enantiomer over the R enantiomer.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, IN 1972).

All methods described herein can be performed in any suitable order unless otherwise indicated herein or otherwise clearly contradicted by context. The use of any and all examples, or exemplary language (e.g. "such as") provided herein is intended merely to better illuminate the disclosure and does not pose a limitation on the scope of the disclosure otherwise claimed.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the disclosure into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

The compounds disclosed herein may also contain unnatural proportions of atomic isotopes at one or more of the atoms that constitute such compounds. For example, the compounds may be radiolabeled with radioactive isotopes, such as for example deuterium ($^{2}H$), tritium ($^{3}H$), carbon-13 ($^{13}C$), or carbon-14 ($^{14}C$). All isotopic variations of the compounds disclosed herein, whether radioactive or not, are intended to be encompassed within the scope of the present disclosure. In addition, all tautomeric forms of the compounds described herein are intended to be within the scope of the disclosure.

The term "tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane that are likewise formed by treatment with acid or base. Tautomeric forms may be relevant to the attainment of the optimal chemical reactivity and biological activity of a compound of interest.

Compounds

In one aspect, the disclosure provides a compound of Formula (I) or a pharmaceutically acceptable salt thereof, wherein:

(I)

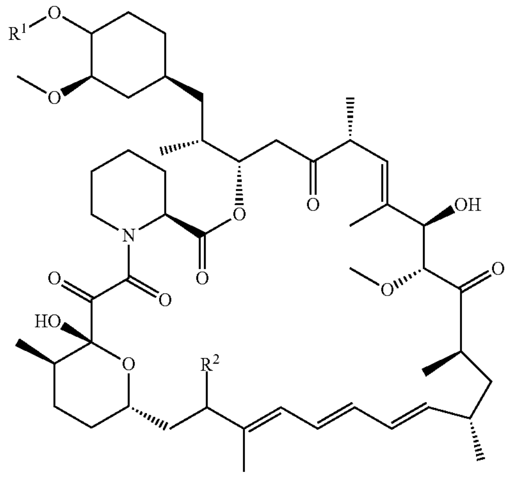

$R^1$ is selected from the group consisting of hydrogen, $C_{1-6}$ alkyl, hydroxyl$C_{1-6}$alkyl, and hetero$C_{1-6}$alkyl; and $R^2$ is

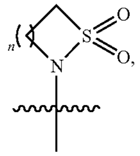

wherein n is 1, 2 or 3.

In an embodiment, $R^1$ is selected from the group consisting of hydroxyl and

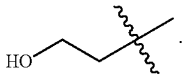

In an embodiment, $R_2$ is

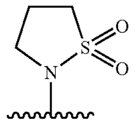

or

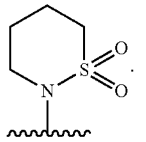

In an embodiment, $R_2$ is

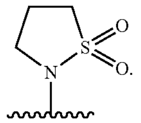 [SMILES: *N1CCCS1(=O)=O]

In an embodiment, $R_2$ is

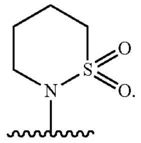 [SMILES: *N1CCCCS1(=O)=O]

In an embodiment, $R^1$ is selected from the group consisting of hydroxyl and

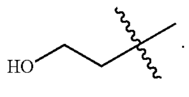

and $R_2$ is

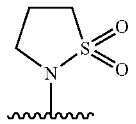

or

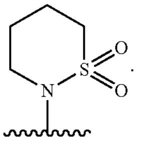

In an embodiment, the compound or pharmaceutically acceptable salt thereof is selected from:
| Compound | Structure |
|---|---|
| 1 | 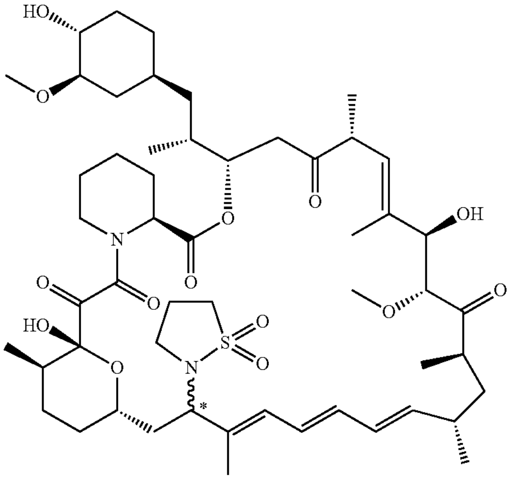 * Absolute sterochemistry at C16 undetermined |
| 2 and 3 | 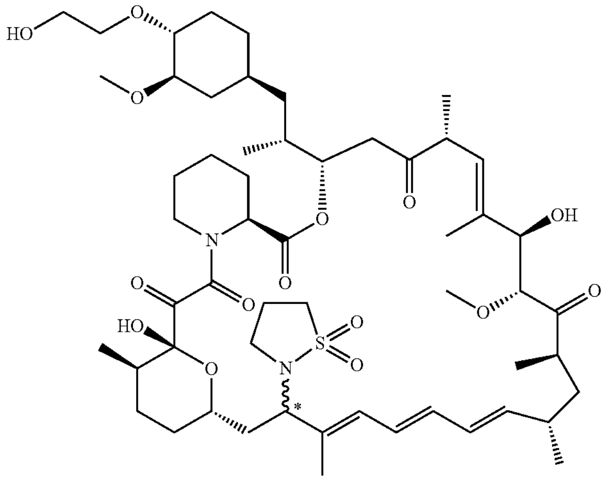 * Absolute sterochemistry at C16 undetermined |
| 4 | 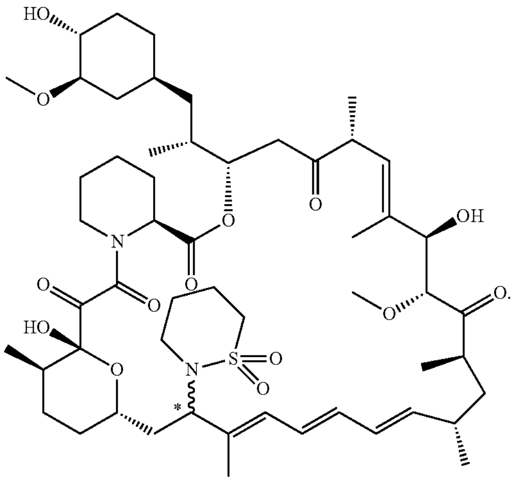 * Absolute sterochemistry at C16 undetermined |

Pharmaceutically Acceptable Salts

Pharmaceutically acceptable salts of these compounds are also contemplated for the uses described herein. As used herein, the terms "salt" or "salts" refer to an acid addition or base addition salt of a compound of the disclosure. "Salts" include in particular "pharmaceutical acceptable salts." The term "pharmaceutically acceptable salts" refers to salts that retain the biological effectiveness and properties of the compounds disclosed herein and, which typically are not biologically or otherwise undesirable. In many cases, the compounds disclosed herein are capable of forming acid and/or base salts by virtue of the presence of amino and/or carboxyl groups or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the disclosure provides a compound of Formula (I) in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

Pharmaceutical Compositions

In another aspect, the disclosure provides a pharmaceutical composition comprising one or more compounds of Formula (I) or a pharmaceutically acceptable salt thereof, and one or more pharmaceutically acceptable carrier. The term "pharmaceutically acceptable carrier" refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compositions of the disclosure may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrastemal, intrathecal, intrahepatic, intralesional and intracranial injection or infusion techniques. In some embodiments, the compositions of the disclosure are administered orally, intraperitoneally or intravenously. Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tween®, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this disclosure may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this disclosure may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs. Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

The pharmaceutically acceptable compositions of this disclosure may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. The amount of the compounds of the present disclosure that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

Isotopically Labelled Compounds

A compound of Formula (I) or a pharmaceutically acceptable salt thereof is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}P$, $^{32}P$, $^{35}S$, $^{36}Cl$, $^{123}I$, $^{124}I$, $^{125}I$, respectively. The disclosure includes various isotopically labeled compounds as defined herein, for example, those into which radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of Formula (I), (Ia) or (Ib) or a pharmaceutically acceptable salt thereof can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^{2}H$ or D) may afford certain therapeutic advantages resulting from greater metabolic stability, for example, increased in vivo half-life or reduced dosage requirements or an improvement in therapeutic index. It is understood that deuterium in this context is regarded as a substituent of a compound of Formula (I) or a pharmaceutically acceptable salt thereof. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of the disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Dosages

Toxicity and therapeutic efficacy of compounds of the disclosure, including pharmaceutically acceptable salts and deuterated variants, can be determined by standard pharmaceutical procedures in cell cultures or experimental animals. The $LD_{50}$ is the dose lethal to 50% of the population. The ED50 is the dose therapeutically effective in 50% of the population. The dose ratio between toxic and therapeutic effects ($LD_{50}/ED_{50}$) is the therapeutic index. Compounds that exhibit large therapeutic indexes are preferred. While compounds that exhibit toxic side effects may be used, care should be taken to design a delivery system that targets such compounds to the site of affected tissue in order to minimize potential damage to uninfected cells and, thereby, reduce side effects.

Data obtained from the cell culture assays and animal studies can be used in formulating a range of dosage for use in humans. The dosage of such compounds may lie within a range of circulating concentrations that include the $ED_{50}$ with little or no toxicity. The dosage may vary within this range depending upon the dosage form employed and the route of administration utilized. For any compound, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans.

Levels in plasma may be measured, for example, by high performance liquid chromatography.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present disclosure in the composition will also depend upon the particular compound in the composition.

All methods described herein can be performed in any suitable order unless otherwise indicated herein or otherwise clearly contradicted by context. The use of any and all examples, or exemplary language (e.g. "such as") provided herein is intended merely to better illuminate the disclosure and does not pose a limitation on the scope of the disclosure otherwise claimed.

Any asymmetric atom (e.g., carbon or the like) of the compound(s) of the disclosure can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(F)-form.

Accordingly, as used herein a compound of the disclosure can be in the form of one of the possible stereoisomers, rotamers, atropisomers, tautomers or mixtures thereof, for example, as substantially pure geometric (cis or trans) stereoisomers, diastereomers, optical isomers (antipodes), racemates or mixtures thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Any resulting racemates of compounds of the disclosure or of intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the disclosure into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds of the disclosure or racemic intermediates can also be resolved by chiral chromatography, e.g., high pressure liquid chromatography (HPLC) using a chiral adsorbent.

Diseases and Disorders

Compounds of Formula (I) are useful in the treatment of a disease or disorder selected from:

Transplant vasculopathies;

Smooth muscle cell proliferation and migration leading to vessel intimal thickening, blood vessel obstruction, obstructive coronary atherosclerosis, restenosis;

Autoimmune diseases and inflammatory conditions;

Asthma;

Multi-drug resistance (MDR);

Fungal infections;

Inflammation;

Infection;

Age-related diseases;

Neurodegenerative diseases;

Proliferative disorders, e.g., cancer;

Seizures and seizure related disorders; and

Mitochondrial myopathy and mitochondrial stress.

In another aspect, a compound disclosed herein can be used to treat conditions which have been shown to make age-related diseases more likely, such as settings where there is an increase in senescence inducing cytokines (e.g. IL6).

In another aspect, a compound disclosed herein can be used to treat disorders that include the process of fibrosis and/or inflammation, e.g., liver and kidney disorders. Examples include, liver fibrosis, which occurs in end-stage liver disease; liver cirrhosis; liver failure due to toxicity; non-alcohol-associated hepatic steatosis or NASH; and alcohol-associated steatosis. Another example is kidney fibrosis, which occurs as a result of acute kidney injury, leading to chronic kidney disease. Diabetic nephropathy can induce kidney fibrosis and inflammation. Often kidney disease causes heart failure, as a result of an increase in blood pressure; this can also be associated with cardiac fibrosis.

In another aspect, the compounds of the disclosure can be used to treat cardiac failure. (Buss, S. J. et al. Beneficial effects of Mammalian target of rapamycin inhibition on left ventricular remodeling after myocardial infarction. J Am Coll Cardiol. (2009) 54(25): 2435-46; Buss, S. J. et al. Augmentation of autophagy by mTOR-inhibition in myocardial infarction: When size matters. Autophagy. (2010) 6(2):304-6.

In another aspect, the compounds of the disclosure can be used to treat liver fibrosis in patients who have undergone liver transplants. (Villamil, F. G. et al. Fibrosis progression in maintenance liver transplant patients with hepatitis C recurrence: a randomized study of RAD001 vs. calcineurin inhibitors. Liver Int. (2014) 34(10):1513-21).

Transplant vasculopathies include atherosclerosis.

Autoimmune diseases and inflammatory conditions include in particular inflammatory conditions with an etiology including an autoimmune component such as arthritis (for example rheumatoid arthritis, arthritis chronica progrediente and arthritis deformans) and rheumatic diseases. Specific autoimmune diseases for which the compounds of Formula (I) may be employed include, autoimmune hematological disorders (including e. g. hemolytic anemia, aplastic anemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, psoriasis, Steven-Johnson syndrome, idiopathic sprue, autoimmune inflammatory bowel disease (including e. g. ulcerative colitis and Crohn's disease) endocrine ophthalmopathy, Graves disease, sarcoidosis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis, glomerulonephritis (with and without nephrotic syndrome, e.g. including idiopathic nephrotic syndrome or minimal change nephropathy) and juvenile dermatomyositis.

Compounds of the disclosure can also be useful in the treatment of multi-drug resistance (MDR), which includes enhancing the efficacy of other chemotherapeutic agents in the treatment and control of multidrug resistant conditions such as multidrug resistant cancer or multidrug resistant AIDS. MDR is particularly problematic in cancer patients and AIDS patients who will not respond to conventional chemotherapy because the medication is pumped out of the cells by Pgp.

Compounds of the disclosure can also be useful in the treatment of infection, which includes infection by pathogens having Mip or Mip-like factors.

Age-related diseases also include: sarcopenia, skin atrophy, cherry angiomas, seborrheic keratoses, brain atrophy (also referred to as dementia), atherosclerosis, arteriosclerosis, pulmonary emphysema, osteoporosis, osteoarthritis, high blood pressure, cataracts, macular degeneration, glaucoma, stroke, cerebrovascular disease (strokes), chronic kidney disease, diabetes-associated kidney disease, impaired hepatic function, liver fibrosis, autoimmune hepatitis, endometrial hyperplasia, metabolic dysfunction, renovascular disease, hearing loss, mobility disability (e.g., frailty), cognitive decline, tendon stiffness, heart dysfunction such as cardiac hypertrophy and/or systolic and/or diastolic dysfunction and/or hypertension and/or dilated cardiomyopathy, heart dysfunction which results in a decline in ejection fraction, immune senescence, Parkinson's disease, Alzheimer's disease, cancer, immune-senescence leading to cancer due to a decrease in immune-surveillance, infections due to an decline in immune-function, chronic obstructive pulmonary disease (COPD), obesity, loss of taste, loss of olfaction, arthritis, and type II diabetes (including complications stemming from diabetes, such as kidney failure, blindness and neuropathy).

Neurodegenerative diseases include Huntington's Disease, Parkinson's disease, spinocerebellar ataxia type 3, Alzheimer's disease, motor neuron disease and peripheral neuropathy.

Proliferative disorders include cancer. Such conditions include those listed in U.S. Pat. No. 9,669,032, e.g., renal cancer, renal cell carcinoma, colorectal cancer, uterine sarcoma, endometrial uterine cancer, endometrial cancer, breast cancer, ovarian cancer, cervical cancer, gastric cancer, fibrosarcoma, pancreatic cancer, liver cancer, melanoma, leukemia, multiple myeloma, nasopharyngeal cancer, prostate cancer, lung cancer, glioblastoma, astrocytoma, adenocarcinoma, bladder cancer, mesothelioma, head cancer, rhabdomyosarcoma, sarcoma, lymphoma, and neck cancer.

Seizures and seizure related disorders include West syndrome, Focal Cortical Dysplasia (FCD), tuberous sclerosis complex (TSC), childhood absence epilepsy, benign focal epilepsies of childhood, juvenile myoclonic epilepsy (JME), temporal lobe epilepsy, frontal lobe epilepsy, refractory epilepsy, Lennox-Gastaut syndrome, occipital lobe epilepsy, Proteus syndrome, hemi-megalencephaly syndrome (HMEG), megalencephaly syndrome (MEG), megalencephaly-capillary malformation (MCAP) and megalencephaly-polymicrogyria-polydactyly-hydrocephalus syndrome (MPPH).

Mitochondrial myopathy and mitochondrial stress are mitochondrial disorders as described in Chinnery, P. F. (2015); EMBO Mol. Med. 7, 1503-1512; Koopman, W. J. et al., (2016); EMBO Mol. Med. 8, 311-327 and Young, M. J., and Yound and Copeland, W. C. (2016); Curr. Opin. Genet. Dev. 38, 52-62.

Treatable conditions which have been shown to make age-related diseases more likely include senescence, e.g., immune senescence. This is diagnosed by (i) an increase in circulating cytokines, such as IL-6, but also by (ii) senescent cells found in muscle, kidney, liver, brain, neurons, liver, pancreas, or the heart; or also (iii) a decline in the efficiency of DNA-repair, which can be shown by an increase in transcription of repetitive elements, including transposon-encoded genes.

Methods of Use

The disclosure provides a compound of Formula (I) or a pharmaceutically acceptable salt thereof for treatment of diseases and disorders described herein, e.g., age-related disorders, or diseases and disorders currently approved for treatment using rapalogs, such as RAD001.

In one aspect, the disclosure provides a method for treating a disorder or a disease mediated by the mTOR pathway in a subject in need thereof, the method comprising administering to the subject a therapeutically effective amount of a compound of Formula (I) or a pharmaceutically acceptable salt thereof.

In another aspect, the disclosure provides a method for treating a disease or disorder in a subject, wherein the target tissue, organ, or cells associated with the pathology of the disease or disorder has FKBP12 levels sufficient to inhibit mTORC1, the method comprising administering to the subject in need thereof a therapeutically effective amount of a compound of Formula (I) or a pharmaceutically acceptable salt thereof.

In another aspect, the disclosure provides a method for treating a disease or disorder in a subject having, or a subject that has been determined to have, FKBP12 levels sufficient to inhibit mTORC1, the method comprising administering to the subject in need thereof a therapeutically effective amount of a compound of Formula (I) or a pharmaceutically acceptable salt thereof.

In an embodiment, the disease or disorder is selected from sarcopenia, skin atrophy, cherry angiomas, seborrheic keratoses, brain atrophy, atherosclerosis, arteriosclerosis, pulmonary emphysema, osteoporosis, osteoarthritis, high blood pressure, cataracts, macular degeneration, glaucoma, stroke, cerebrovascular disease (strokes), chronic kidney disease, diabetes-associated kidney disease, impaired hepatic function, liver fibrosis, autoimmune hepatitis, endometrial hyperplasia, metabolic dysfunction, renovascular disease, hearing loss, mobility disability, cognitive decline, tendon stiffness, heart dysfunction, such as cardiac hypertrophy, systolic or diastolic dysfunction, hypertension, dilated cardiomyopathy, heart dysfunction which results in a decline in ejection fraction, immune senescence, Parkinson's disease, Alzheimer's disease, cancer, immune-senescence leading to cancer due to a decrease in immune-surveillance, infections due to an decline in immune-function, chronic obstructive pulmonary disease (COPD), obesity, loss of taste, loss of olfaction, arthritis, and type II diabetes including complications stemming from diabetes, such as kidney failure, blindness and neuropathy.

In an embodiment, the disorder is liver fibrosis.

In another aspect, the disclosure provides a method of treating a disease or disorder in a subject in need thereof, the method comprising administering to the subject a therapeutically effective amount of a compound of Formula (I) or a pharmaceutically acceptable salt thereof, a pharmaceutical composition comprising a compound of Formula (I) or a pharmaceutically acceptable salt thereof, or a pharmaceutical combination comprising a compound of Formula (I) or a pharmaceutically acceptable salt thereof, wherein the disorder or disease is selected from:

Transplant vasculopathies;

Smooth muscle cell proliferation and migration leading to vessel intimal thickening, blood vessel obstruction, obstructive coronary atherosclerosis, restenosis;

Autoimmune diseases and inflammatory conditions;

Asthma;

Multi-drug resistance (MDR);

Fungal infections;

Inflammation;

Infection;

Age-related diseases;

Neurodegenerative diseases;

Proliferative disorders, in particular cancer;

Seizures and seizure related disorders; and

Mitochondrial myopathy and mitochondrial stress.

In an embodiment, the disorder is a disorder that includes the process of fibrosis and/or inflammation.

In an embodiment, the disorder is selected from liver and kidney disorders.

In an embodiment, the liver disorder is selected from: liver fibrosis, which occurs in end-stage liver disease; liver cirrhosis; liver failure due to toxicity; non-alcohol-associated hepatic steatosis or NASH; and alcohol-associated steatosis.

In an embodiment, the kidney disorder is kidney fibrosis.

In an embodiment, the kidney fibrosis occurs as a result of acute kidney injury.

In an embodiment, the kidney disorder is chronic kidney disorder.

In an embodiment, the kidney disorder is diabetic nephropathy.

In another aspect, the disclosure provides a method of treating an age-related disorder or disease in a subject in need thereof, the method comprising administering to the subject a therapeutically effective amount of a compound of Formula (I) or a pharmaceutically acceptable salt thereof, a pharmaceutical composition comprising a compound of Formula (I) or a pharmaceutically acceptable salt thereof, or a pharmaceutical combination comprising a compound of Formula (I) or a pharmaceutically acceptable salt thereof, wherein the disorder or disease is selected from: sarcopenia, skin atrophy, cherry angiomas, seborrheic keratoses, brain atrophy, atherosclerosis, arteriosclerosis, pulmonary emphysema, osteoporosis, osteoarthritis, high blood pressure, cataracts, macular degeneration, glaucoma, stroke, cerebrovascular disease (strokes), chronic kidney disease, diabetes-associated kidney disease, impaired hepatic function, liver fibrosis, autoimmune hepatitis, endometrial hyperplasia, metabolic dysfunction, renovascular disease, hearing loss, mobility disability, cognitive decline, tendon stiffness, heart dysfunction such as cardiac hypertrophy and/or systolic and/or diastolic dysfunction and/or hypertension, heart dysfunction which results in a decline in ejection fraction, immune senescence, Parkinson's disease, Alzheimer's disease, cancer, immune-senescence leading to cancer due to a decrease in immune-surveillance, infections due to an decline in immune-function, chronic obstructive pulmonary disease (COPD), obesity, loss of taste, loss of olfaction, arthritis, and type II diabetes including complications stemming from diabetes, such as kidney failure, blindness and neuropathy.

In another aspect, the disclosure provides a method of treating cancer in a subject, the method comprising administering to the subject a therapeutically effective amount of a compound of Formula (I) or a pharmaceutically acceptable salt thereof, a pharmaceutical composition comprising a compound of Formula (I) or a pharmaceutically acceptable salt thereof, or a pharmaceutical combination comprising a compound of Formula (I) or a pharmaceutically acceptable salt thereof.

In an embodiment, the method further comprises a PD-1/PDL-1 inhibitor.

In an embodiment, the cancer is selected from renal cancer, renal cell carcinoma, colorectal cancer, uterine sarcoma, endometrial uterine cancer, endometrial cancer, breast cancer, ovarian cancer, cervical cancer, gastric cancer, fibrosarcoma, pancreatic cancer, liver cancer, melanoma, leukemia, multiple myeloma, nasopharyngeal cancer, prostate cancer, lung cancer, glioblastoma, bladder cancer, mesothelioma, head cancer, rhabdomyosarcoma, sarcoma, lymphoma, and neck cancer.

In another aspect, the disclosure provides a compound of Formula (I) or a pharmaceutically acceptable salt thereof, a pharmaceutical composition comprising a compound of Formula (I) or a pharmaceutically acceptable salt thereof, or a pharmaceutical combination comprising a compound of Formula (I) or a pharmaceutically acceptable salt thereof, for use as a medicament.

In another aspect, the disclosure provides a compound of Formula (I) or a pharmaceutically acceptable salt thereof, a pharmaceutical composition comprising a compound of Formula (I) or a pharmaceutically acceptable salt thereof, or a pharmaceutical combination comprising a compound of Formula (I) or a pharmaceutically acceptable salt thereof, for use in the prevention or treatment of a disorder or disease mediated by the mTOR pathway.

In another aspect, the disclosure provides a compound of Formula (I) or a pharmaceutically acceptable salt thereof, a pharmaceutical composition comprising a compound of Formula (I) or a pharmaceutically acceptable salt thereof, or a pharmaceutical combination comprising a compound of Formula (I) or a pharmaceutically acceptable salt thereof, for use in the prevention or treatment of a disorder or disease selected from:

Transplant vasculopathies;

Smooth muscle cell proliferation and migration leading to vessel intimal thickening, blood vessel obstruction, obstructive coronary atherosclerosis, restenosis;

Autoimmune diseases and inflammatory conditions;

Asthma;

Multi-drug resistance (MDR);

Fungal infections;

Inflammation;

Infection;

Age-related diseases;

Neurodegenerative diseases;

Proliferative disorders, in particular cancer;

Seizures and seizure related disorders; and

Mitochondrial myopathy and mitochondrial stress.

In another aspect, the disclosure provides a compound of Formula (I) or a pharmaceutically acceptable salt thereof, a pharmaceutical composition comprising a compound of Formula (I) or a pharmaceutically acceptable salt thereof, or a pharmaceutical combination comprising a compound of Formula (I) or a pharmaceutically acceptable salt thereof, for use in the prevention or treatment of a disorder or disease that includes the process of fibrosis and/or inflammation.

In an embodiment, the disorder is selected from liver and kidney disorders.

In an embodiment, the liver disorder is selected from: liver fibrosis, which occurs in end-stage liver disease; liver cirrhosis; liver failure due to toxicity; non-alcohol-associated hepatic steatosis or NASH; and alcohol-associated steatosis.

In an embodiment, the kidney disorder is kidney fibrosis, which occurs as a result of acute kidney injury.

In an embodiment, the kidney disorder is chronic kidney disorder.

In an embodiment, the kidney disorder is diabetic nephropathy.

In another aspect, the disclosure provides a compound of Formula (I) or a pharmaceutically acceptable salt thereof, a pharmaceutical composition comprising a compound of Formula (I) or a pharmaceutically acceptable salt thereof, or a pharmaceutical combination comprising a compound of Formula (I) or a pharmaceutically acceptable salt thereof, for use in the treatment of an age-related disorder or disease selected from sarcopenia, skin atrophy, cherry angiomas, seborrheic keratoses, brain atrophy (also referred to as dementia), atherosclerosis, arteriosclerosis, pulmonary emphysema, osteoporosis, osteoarthritis, high blood pressure, cataracts, macular degeneration, glaucoma, stroke, cerebrovascular disease (strokes), chronic kidney disease, diabetes-associated kidney disease, impaired hepatic function, liver fibrosis, autoimmune hepatitis, endometrial hyperplasia, metabolic dysfunction, renovascular disease, hearing loss, mobility disability (e.g., frailty), cognitive decline, tendon stiffness, heart dysfunction such as cardiac hypertrophy and/or systolic and/or diastolic dysfunction and/or hypertension and/or dilated cardiomyopathy, heart dysfunction which results in a decline in ejection fraction, immune senescence, Parkinson's disease, Alzheimer's disease, cancer, immune-senescence leading to cancer due to a decrease in immune-surveillance, infections due to an decline in immune-function, chronic obstructive pulmonary disease (COPD), obesity, loss of taste, loss of olfaction, arthritis, and type II diabetes (including complications stemming from diabetes, such as kidney failure, blindness and neuropathy).

In another aspect, the disclosure provides a compound of Formula (I) or a pharmaceutically acceptable salt thereof, a pharmaceutical composition comprising a compound of Formula (I) or a pharmaceutically acceptable salt thereof, or a pharmaceutical combination comprising a compound of Formula (I) or a pharmaceutically acceptable salt thereof, for use in the treatment of cancer.

In another aspect, the disclosure provides a compound of Formula (I) or a pharmaceutically acceptable salt thereof, a pharmaceutical composition comprising a compound of Formula (I) or a pharmaceutically acceptable salt thereof, or a pharmaceutical combination comprising a compound of Formula (I) or a pharmaceutically acceptable salt thereof, for use in the treatment of renal cancer, renal cell carcinoma, colorectal cancer, uterine sarcoma, endometrial uterine cancer, endometrial cancer, breast cancer, ovarian cancer, cervical cancer, gastric cancer, fibro-sarcoma, pancreatic cancer, liver cancer, melanoma, leukemia, multiple myeloma, nasopharyngeal cancer, prostate cancer, lung cancer, glioblastoma, bladder cancer, mesothelioma, head cancer, rhabdomyosarcoma, sarcoma, lymphoma, or neck cancer.

In another aspect, the disclosure provides a use of a compound of Formula (I) or a pharmaceutically acceptable salt thereof for the manufacture of a medicament.

In another aspect, the disclosure provides a use of a compound of Formula (I) or a pharmaceutically acceptable salt thereof for the manufacture of a medicament for the treatment of a disorder or disease mediated by the mTOR pathway.

In another aspect, the disclosure provides a use of a compound of Formula (I) or a pharmaceutically acceptable salt thereof for the manufacture of a medicament for the treatment of a disorder or disease selected from:

Transplant vasculopathies;

Smooth muscle cell proliferation and migration leading to vessel intimal thickening, blood vessel obstruction, obstructive coronary atherosclerosis, restenosis;

Autoimmune diseases and inflammatory conditions;

Asthma;

Multi-drug resistance (MDR);

Fungal infections;

Inflammation;

Infection;

Age-related diseases;

Neurodegenerative diseases;

Proliferative disorders, e.g., cancer;

Seizures and seizure related disorders; and

Mitochondrial myopathy and mitochondrial stress.

In another aspect, the disclosure provides a use of a compound of Formula (I) or a pharmaceutically acceptable salt thereof for the manufacture of a medicament for the treatment of a disorder or disease that includes the process of fibrosis or inflammation.

In an embodiment, the disorder is selected from liver and kidney disorders.

In an embodiment, the liver disorder is selected from: liver fibrosis, which occurs in end-stage liver disease; liver cirrhosis; liver failure due to toxicity; non-alcohol-associated hepatic steatosis or NASH; and alcohol-associated steatosis.

In an embodiment, the kidney disorder is kidney fibrosis, which occurs as a result of acute kidney injury.

In an embodiment, the kidney disorder is chronic kidney disorder.

In an embodiment, the kidney disorder is diabetic nephropathy.

In another aspect, the disclosure provides a use of a compound of Formula (I) or a pharmaceutically acceptable salt thereof for the manufacture of a medicament for the manufacture of a medicament for the prevention or treatment of an age-related disorder or disease selected from sarcopenia, skin atrophy, cherry angiomas, seborrheic keratoses, brain atrophy (also referred to as dementia), atherosclerosis, arteriosclerosis, pulmonary emphysema, osteoporosis, osteoarthritis, high blood pressure, cataracts, macular degeneration, glaucoma, stroke, cerebrovascular disease (strokes), chronic kidney disease, diabetes-associated kidney disease, impaired hepatic function, liver fibrosis, autoimmune hepatitis, endometrial hyperplasia, metabolic dysfunction, renovascular disease, hearing loss, mobility disability, cognitive decline, tendon stiffness, heart dysfunction such as cardiac hypertrophy and/or systolic and/or diastolic dysfunction and/or hypertension and/or dilated cardiomyopathy, heart dysfunction which results in a decline in ejection fraction, immune senescence, Parkinson's disease, Alzheimer's disease, cancer, immune-senescence leading to cancer due to a decrease in immune-surveillance, infections due to an decline in immune-function, chronic obstructive pulmonary disease (COPD), obesity, loss of taste, loss of olfaction, arthritis, and type II diabetes (including complications stemming from diabetes, such as kidney failure, blindness and neuropathy).

In another aspect, the disclosure provides a use of a compound of Formula (I) or a pharmaceutically acceptable salt thereof for the manufacture of a medicament for the manufacture of a medicament for the prevention or treatment of cancer.

In another aspect, the disclosure provides a use of a compound of Formula (I) or a pharmaceutically acceptable salt thereof for the manufacture of a medicament for the manufacture of a medicament for the treatment of renal cancer, renal cell carcinoma, colorectal cancer, uterine sarcoma, endometrial uterine cancer, endometrial cancer, breast cancer, ovarian cancer, cervical cancer, gastric cancer, fibrosarcoma, pancreatic cancer, liver cancer, melanoma, leukemia, multiple myeloma, nasopharyngeal cancer, prostate cancer, lung cancer, glioblastoma, bladder cancer, mesothelioma, head cancer, rhabdomyosarcoma, sarcoma, lymphoma, or neck cancer.

Methods of Making a Compound of Formula (I)

In another aspect, the disclosure provides a method of making a compound of the disclosure according to Schemes 1 and 2.

Scheme 1

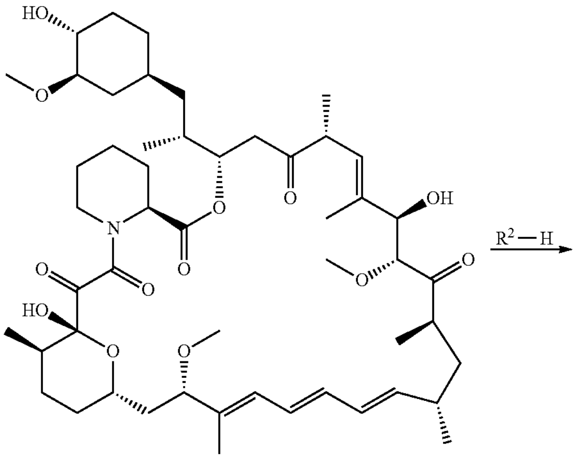

rapamycin

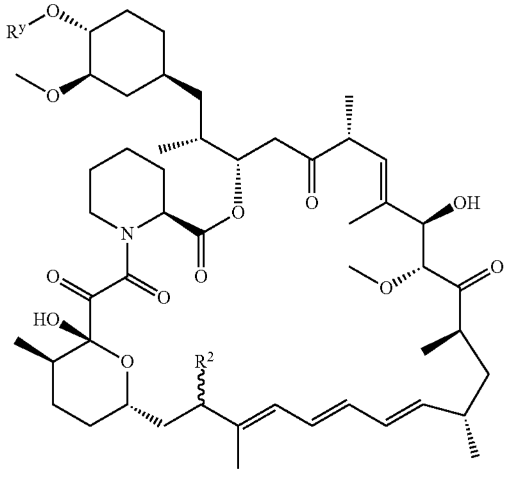

Formula (I)

A compound of Formula (I), wherein $R^1$ is hydrogen and $R^2$ is as defined under Formula (I), may be obtained by reacting rapamycin with $R^2$—H, wherein $R^2$ is as defined under Formula (I), in the presence of a suitable reagent for a substitution reaction, e.g. p-toluenesulphonic acid, in the presence of a suitable solvent, e.g. dichloromethane. For example, suitable conditions are as follows:

1) $R_2$—H, p-toluenesulphonic acid-$H_2O$, dichloromethane, room temperature
2) $R_2$—H, trifluoroacetic acid, −40° C., dichloromethane (see EP1212331B1)
3) $R_2$—H, 5M $LiClO_4$, $Et_2O$ (0.1M), room temperature (see TL, 1995, 43, 7823)
4) $R_2$—H, $Cp_2HfCl_2$—$AgClO_4$ (Suzuki's catalyst), 4A MS, dichloromethane, room temperature (see TL, 1995, 43, 7823)
5) $R_2$—H, $BF_3$-$OEt_2$ or $Zn(OTf)_2$, THF, 0° C. (see TL, 1994, 37, 6835)
6) $R_2$—H, $ZnCl_2$, dichloromethane, 0° C. (see JOC, 1994, 59, 6512).

Scheme 2

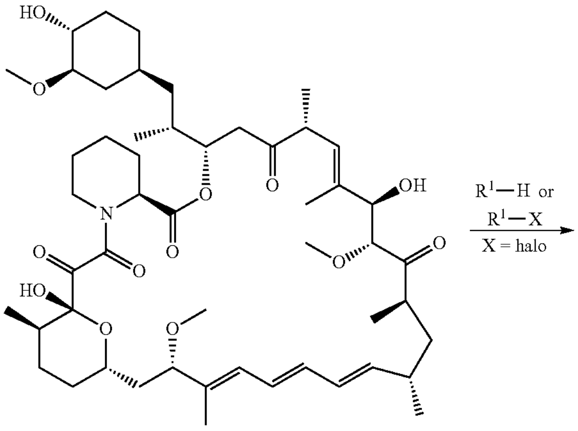

rapamycin

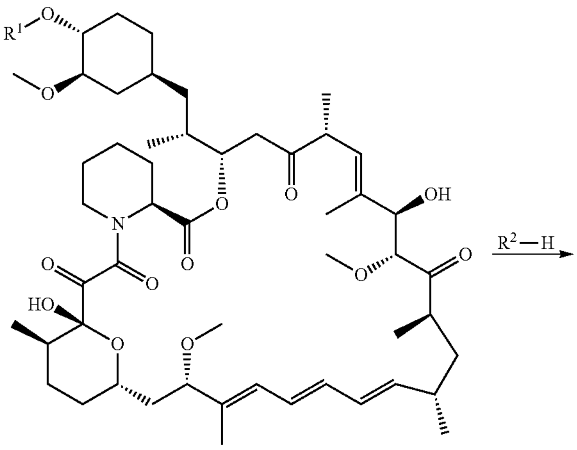

Intermediate 1

-continued

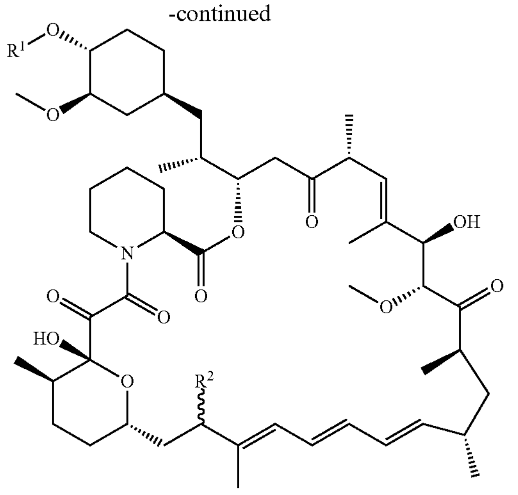

Formula (I)

A compound of Formula (I), wherein $R^1$ is selected from the group consisting of $C_{1-6}$alkyl, hydroxyl$C_{1-6}$alkyl, and hetero$C_{1-6}$alkyl; and $R^2$ is as defined under Formula (I), may be obtained by reacting rapamycin with $R^1$—H or $R^1$—X to provide Intermediate 1 followed by reaction with $R^2$—H. In an embodiment, rapamycin is reacted with $R^1$—H or $R^1$—X under alkylation conditions to provide Intermediate 1. In an embodiment, Intermediate 1 is reacted with $R^2$—H under substitution reaction conditions, e.g., as provided herein, to afford a compound of Formula (I).

EXAMPLES

The disclosure sets for the following examples. The synthetic and biological examples described in this application are offered to illustrate the compounds, pharmaceutical compositions, and methods provided herein and are not to be construed in any way as limiting their scope.

The compounds provided herein can be prepared from readily available starting materials using modifications to the specific synthesis protocols set forth below that would be well known to those of skill in the art. It will be appreciated that where typical or preferred process conditions (i.e., reaction temperatures, times, mole ratios of reactants, solvents, pressures, etc.) are given other process conditions can also be used unless otherwise stated. Optimum reaction conditions may vary with the particular reactants or solvents used, but such conditions can be determined by those skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in Greene et al., *Protecting Groups in Organic Synthesis*, Second Edition, Wiley, New York, 1991, and references cited therein.

Rapamycin and its derivatives, for example, compounds of Formula (I), exist as a solvent and pH dependent equilibrium of six-membered and seven-membered hemi-ketal forms shown below as A, B, and C (Scheme 3). See *The Journal of Antibiotics* (Tokyo) (1991) 44(6):688-90; and *Tetrahedron Letters* (1992) 33(33):4139-4142. Rapamycin and its derivatives also exist as a mixture of cis- and trans-amides shown below as A and C. [See Mierke, D. F., Schmieder, P., Karuso, P. and Kessler, H. (1991), Conformational Analysis of the cis- and trans-Isomers of F1006 by NMR and Molecular Dynamics. *Helvetica Chimica Acta,* 74: 1027-1047.] The NMR characterization data shown in the examples corresponds only to the major equilibrium form observed under the reported deutero solvent conditions.

Scheme 3

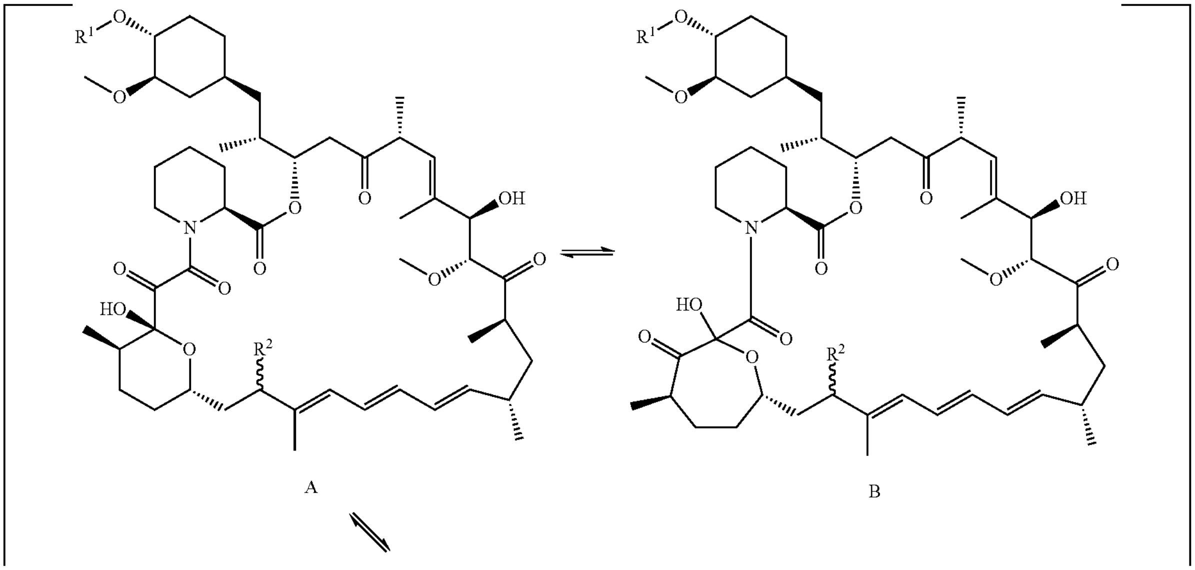

-continued

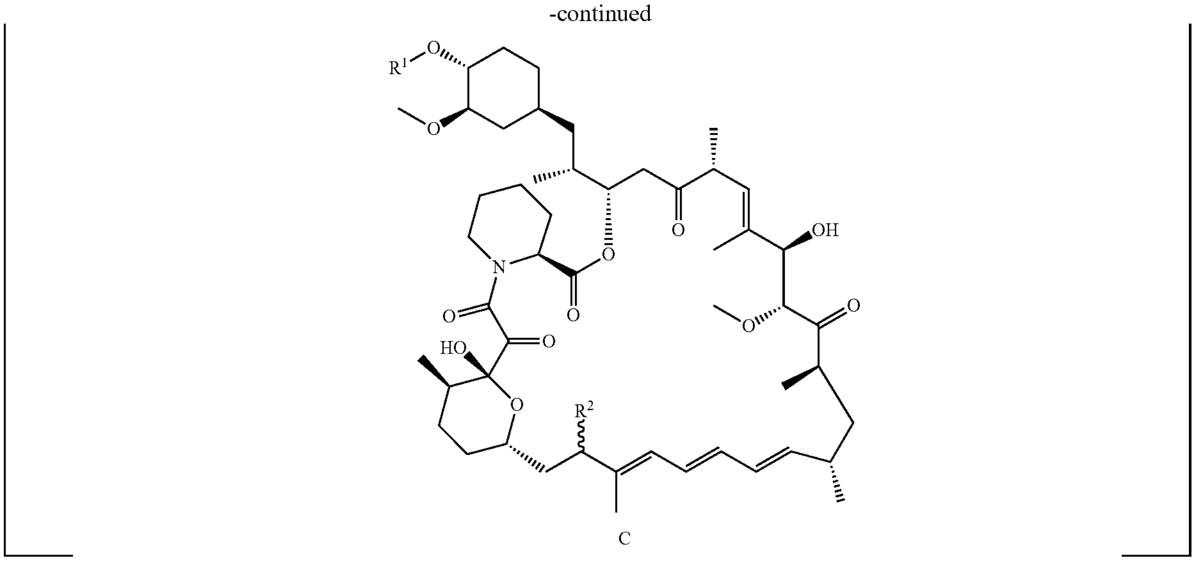

wherein:

$R^1$ is selected from the group consisting of hydrogen, $C_{1-6}$alkyl, hydroxyl$C_{1-6}$alkyl, and hetero$C_{1-6}$alkyl; and $R^2$ is

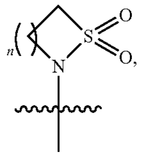

wherein n is 1, 2 or 3.

Preparation of Compounds

Compounds of the disclosure can be prepared as described in the following Examples.

LIST OF ABBREVIATIONS

The following abbreviations used herein below have the corresponding meanings:

A angstrom
Cat. catalytic
ACN acetonitrile
d doublet
dd doublet of doublets
DCM dichloromethane
DMSO dimethylsulfoxide
ESIMS electrospray ionisation mass spectrometry
EtOAc ethyl acetate
eq equivalent
FA formic acid
HSQC NMR Heteronuclear Single Quantum Coherence nuclear magnetic resonance
HPLC high performance liquid chromatography
HRMS high resolution mass spectrometry
h hours
Hz hertz
MeCN acetonitrile
MeOH methanol
M molar
m multiplet
mg milligram
MHz megahertz
mL milliliter(s)
min. minutes
mmol millimole
NMR nuclear magnetic resonance
PEI Polyethylenimine
PPU Propyl-pyridyl-urea
q quartet
rt room temperature
μL microliter(s)
μM micromolar
s singlet
SFC Supercritical Fluid Chromatography
TLC thin layer chromatography
t triplet
TsOH para-toluenesulfonic acid monohydrate Methods Employed in the Purification of the Examples Purification of intermediates and final products was carried out via either normal or reverse phase chromatography.

Flash Chromatography

Normal phase chromatography was carried out using prepacked $SiO_2$ cartridges (e.g., RediSep® Rf columns from Teledyne Isco, Inc.) eluting with gradients of appropriate solvent systems (e.g., hexanes and ethyl acetate; DCM and MeOH; or unless otherwise indicated).

Example 1. Synthesis of Compound 1

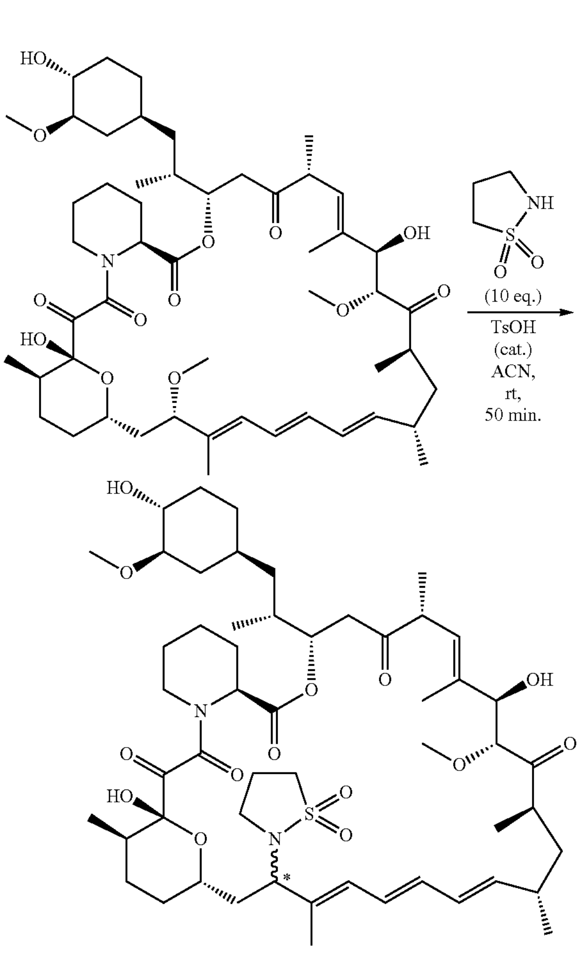

*Absolute stereochemistry at C16 undetermined
Compound 1

Rapamycin (0.549 g, 0.601 mmol) was combined with isothiazolidine 1,1-dioxide (0.728 g, 6.01 mmol) in anhydrous acetonitrile (3.0 mL) in a reaction vial. TsOH (0.011 g, 0.060 mmol) was added and the reaction mixture was stirred at room temperature for 50 minutes. The reaction mixture was diluted with brine and was extracted three times with EtOAc. The organic extracts were combined, dried over $Na_2SO_4$, decanted and concentrated to give a yellow oil crude product (~1 g). The crude product was purified by silica gel flash column chromatography (0 to 50% acetone-heptane, ISCO combiflash gradient elution, 40 g Silicycle silica gel 15-40 um FLH-R10017B-ISO40, TLC 40% acetone-heptane, visualize under UV). Product containing fractions were checked by LCMS, and the fractions with highest purity were combined and concentrated to give Compound 1 (0.315 g, 0.298 mmol, 49.7% yield) as a white solid Compound 1: ESIMS $[M+NH_4]^+$ 1020.7, $[M+H]^-$ 1001.8 HRMS: [M+Na]+ 1025.5367.

$^1H$ NMR (400 MHz, Chloroform-d) δ 6.39 (dd, J=14.7, 10.7 Hz, 1H), 6.22 (dd, J=14.7, 10.6 Hz, 1H), 6.07 (dd, J=14.9, 10.6 Hz, 1H), 6.00 (d, J=10.9 Hz, 1H), 5.40 (d, J=10.0 Hz, 1H), 5.33 (dd, J=14.8, 9.8 Hz, 1H), 5.24-5.17 (m, 1H), 5.00 (td, J=5.9, 3.5 Hz, 1H), 4.57 (dd, J=10.8, 2.4 Hz, 2H), 4.27 (d, J=3.8 Hz, 1H), 4.05-3.94 (m, 2H), 3.63-3.48 (m, 2H), 3.39 (s, 3H), 3.33 (s, 4H), 3.30-3.16 (m, 2H), 3.11-2.98 (m, 2H), 2.98-2.85 (m, 2H), 2.68 (dd, J=17.5, 6.5 Hz, 1H), 2.52 (dd, J=17.3, 5.4 Hz, 1H), 2.47-2.38 (m, 2H), 2.38-2.31 (m, 1H), 2.31-2.25 (m, 2H), 2.23-2.15 (m, 1H), 1.99 (m, 2H), 1.92-1.85 (m, 1H), 1.82 (m, 5H), 1.76-1.70 (m, 6H), 1.64 (m, 4H), 1.58-1.43 (m, 3H), 1.40 (m, 1H), 1.34 (m, 1H), 1.25 (m, 2H), 1.18-1.11 (m, 1H), 1.11-1.00 (m, 10H), 1.00-0.84 (m, 7H), 0.57 (q, J=11.9 Hz, 1H).

Example 2. Synthesis of Compounds 2 and 3

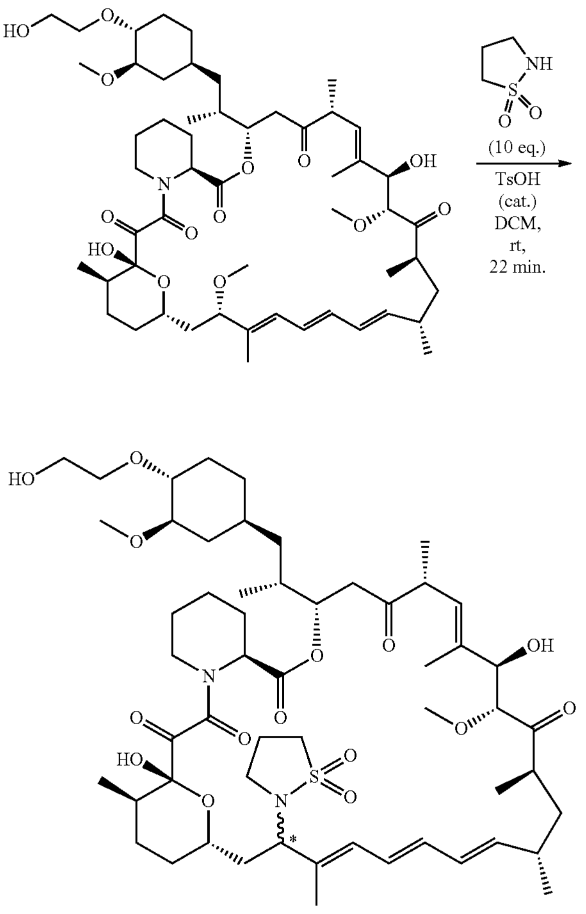

*Absolute stereochemistry at C16 undetermined
Compounds 2 and 3

RAD001 (Everolimus, 1.0 g, 1.044 mmol) was combined with isothiazolidine 1,1-dioxide (1.264 g, 10.44 mmol) in anhydrous dichloromethane (5.2 mL) in a reaction vial. TsOH (0.020 g, 0.104 mmol) was added in one portion. The reaction was stirred at room temperature for 22 minutes.

The reaction mixture was diluted with saturated aqueous NaHCO3 and then was extracted four times with EtOAc. The organic extracts were combined, dried over Na2SO4, decanted and concentrated to give an orange tar crude product (2.181 g).

A portion (1.436 g) of the crude product was purified by silica gel flash column chromatography (15 to 50% acetone-heptane, ISCO combiflash gradient elution, 40 g Silicycle silica gel 15-40 um FLH-R10017B-ISO40, TLC 40% acetone-heptane, visualize under UV). Two spots were observed eluting via TLC.

Product containing fractions were checked by LCMS, and the fractions from the first eluting peak with the highest purity were combined and concentrated to give Compound 2 (0.080 g, 0.073 mmol, 6.95% yield) as a white solid.

Compound 2: ESIMS $[M+NH_4]^+$ 1064.8, $[M+H]^-$ 1046.3.

HRMS: Experimental value from C55H86N2O15SNa: 1069.5248.

$^1$H NMR (400 MHz, Chloroform-d) δ 6.45-6.24 (m, 2H), 6.13 (dd, J=15.1, 9.7 Hz, 1H), 5.96 (d, J=9.8 Hz, 1H), 5.62 (dd, J=15.1, 8.6 Hz, 1H), 5.48-5.37 (m, 1H), 5.30 (d, J=5.9 Hz, 1H), 5.20 (s, 1H), 5.14 (q, J=5.9 Hz, 1H), 4.14 (d, J=6.5 Hz, 1H), 3.88-3.72 (m, 3H), 3.72-3.65 (m, 2H), 3.62-3.56 (m, 2H), 3.50-3.47 (m, 1H), 3.45-3.38 (m, 5H), 3.33 (s, 3H), 3.28-3.04 (m, 6H), 3.04-2.89 (m, 2H), 2.89-2.71 (m, 1H), 2.71 (d, J=5.6 Hz, 1H), 2.34-2.21 (m, 4H), 2.14-2.08 (m, 1H), 2.07-1.98 (m, 2H), 1.97-1.83 (m, 3H), 1.82 (m, 1H), 1.77-1.69 (m, 7H), 1.63-1.48 (m, 4H), 1.44-1.37 (m, 3H), 1.34-1.18 (m, 5H), 1.14-1.09 (dd, J=6.8, 2.9 Hz, 4H), 1.08-0.83 (m, 14H), 0.75-0.64 (m, 1H).

Product containing fractions were checked by LCMS, and the fractions from the second eluting peak with the highest purity were combined and concentrated to give Compound 3 (0.085 g, 0.077 mmol, 7.39%) as a white solid.

Compound 3: ESIMS $[M+NH_4]^+$ 1064.7, $[M+H]^-$ 1046.1.

HRMS: Experimental value from C55H86N2O15SNa: 1069.5630.

$^1$H NMR (400 MHz, Chloroform-d) δ 6.39 (dd, J=14.7, 10.8 Hz, 1H), 6.22 (dd, J=14.7, 10.6 Hz, 1H), 6.07 (dd, J=14.9, 10.6 Hz, 1H), 6.00 (d, J=10.8 Hz, 1H), 5.41 (dt, J=10.0, 1.5 Hz, 1H), 5.33 (dd, J=14.9, 9.8 Hz, 1H), 5.23-5.17 (m, 1H), 5.00 (m, 1H), 4.59-4.51 (m, 2H), 4.27 (m, 1H), 4.04-3.94 (m, 2H), 3.81-3.72 (m, 1H), 3.69 (m, 2H), 3.63-3.49 (m, 3H), 3.43 (s, 3H), 3.32 (s, 3H), 3.28-2.89 (m, 6H), 2.68 (dd, J=17.4, 6.4 Hz, 1H), 2.55-2.23 (m, 8H), 2.19 (d, J=16.0 Hz, 1H), 2.05-1.97 (m, 2H), 1.92-1.77 (m, 5H), 1.76-1.68 (m, 6H), 1.68-1.58 (m, 4H), 1.57-1.47 (m, 2H), 1.47-1.34 (m, 2H), 1.33-1.20 (m, 3H), 1.16-1.10 (m, 1H), 1.04 (t, J=6.5 Hz, 7H), 0.99-0.84 (m, 11H), 0.64 (q, J=12.0 Hz, 1H).

Example 3. Synthesis of Compound 4

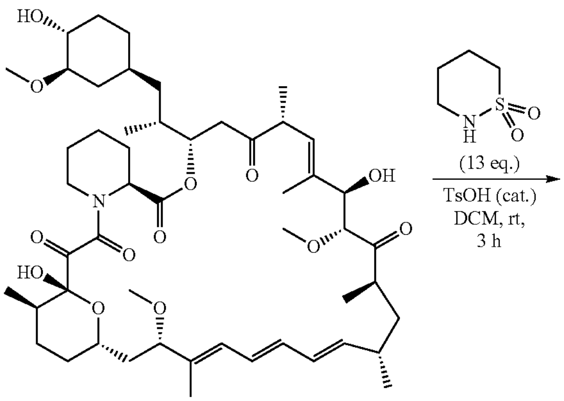

-continued

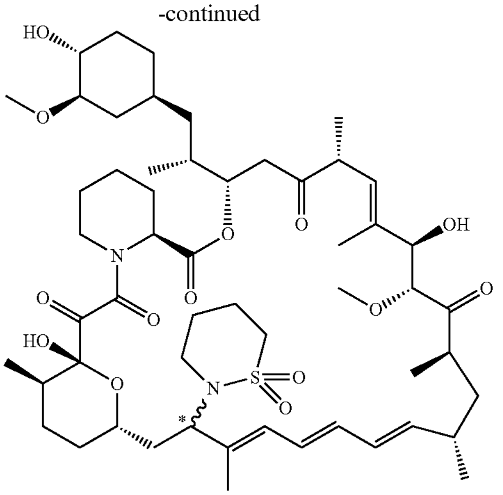

*Absolute stereochemistry at C16 undetermined

Compound 4

Rapamycin (0.464 g, 0.508 mmol) was combined with 1,4-butane sultam (0.892 g, 6.60 mmol) in a reaction vial. The solids were dissolved into anhydrous dichloromethane (2.5 mL). TsOH (9.65 mg, 0.051 mmol) was added in one portion. The reaction was stirred at room temperature for three hours.

The reaction was diluted with saturated aqueous NaHCO3 and was extracted four times with EtOAc. The organic extracts were combined, dried over Na2SO4, vacuum filtered through celite, and concentrated to give a orange-yellow solid crude product (~1.2 g).

The crude product was purified by silica gel flash column chromatography (0-70% acetone-heptane, Isco CombiFlash gradient elution, 40 g RediSep GOLD silica column, TLC in 50% acetone-heptane, visualize under UV) to give Compound 4 (0.060 g, 0.056 mmol, 11.0% yield) as a yellow solid.

Compound 4: ESIMS $[M+NH_4]^+$ 1037.7, $[M+H]^-$ 1015.7.

HRMS: Experimental value from C54H84N2O14SNa: 1039.5544.

$^1$H NMR (600 MHz, Chloroform-d) δ 6.38 (dd, J=14.8, 10.8 Hz, 1H), 6.22 (dd, J=14.8, 10.6 Hz, 1H), 6.07 (dd, J=15.0, 10.6 Hz, 1H), 5.96 (d, J=10.8 Hz, 1H), 5.37 (d, J=10.1 Hz, 1H), 5.33 (dd, J=15.0, 9.9 Hz, 1H), 5.19 (d, J=5.6 Hz, 1H), 5.06 (dt, J=9.7, 4.4 Hz, 1H), 4.84-4.78 (m, 1H), 4.30 (t, J=2.4 Hz, 1H), 4.18 (s, 1H), 4.07 (m, 1H), 4.03 (m, 1H), 3.66 (d, J=13.9 Hz, 1H), 3.39 (s, 3H), 3.37-3.29 (m, 5H), 3.22 (dq, J=10.1, 6.6 Hz, 1H), 3.16-3.12 (m, 1H), 3.09-3.04 (m, 1H), 3.02-2.97 (m, 2H), 2.96-2.89 (m, 1H), 2.69 (dd, J=17.7, 5.5 Hz, 1H), 2.45-2.38 (m, 2H), 2.33-2.16 (m, 5H), 2.04-1.94 (m, 2H), 1.82 (s, 3H), 1.81-1.68 (m, 8H), 1.65-1.59 (m, 7H), 1.56-1.42 (m, 4H), 1.41-1.20 (m, 5H), 1.13-0.96 (m, 9H), 0.93 (dd, J=8.9, 6.6 Hz, 6H), 0.88 (m, 3H), 0.57 (q, J=11.9 Hz, 1H).

Example 4. Biological Assays and Data

The activity of a compound according to the disclosure was assessed by the following in vitro methods.

Pharmacological Characterization

Materials and Methods

Cell-based assay for rapalog potency determination. Rapalog potency was determined using MEF TSC1−/− cell based assay. MEF TSC1−/− cells are Mouse Embryonic Fibroblasts deficient in Tuberous Sclerosis Complex 1-TSC1, which negatively regulates mTORC1 signaling and thus display constitutive mTORC1 activation, resulting in phosphorylation (activation) of downstream molecules. This cell-based assay is used to measure inhibition (de-phosphorylation) of S6 and 4EBP1 by rapalogs or other mTOR inhibitors.

MEF TSC1−/− cells were plated on Poly-D-lysine coated 384 well Griener clear bottom plates and incubated overnight at 37° C., 5% $CO_2$. On the following day, cells were washed 8 times with "Hard starve" solution (1 L DPBS+1 g D-(+) glucose+10 ml of 7.5% Sodium Bicarbonate+20 ml of 1M HEPES) and incubated for further 2 hours in the same solution. Cells were next treated with compounds with decreasing concentrations (8 points at 3.16 fold dilutions) and incubated for 2 hours at 37° C., 5% $CO_2$. Cells were fixed with 4% paraformaldehyde for 30 min and washed 5 times with TBS-EDTA followed by immuno-staining with fluorescent tag labeled antibodies for pS6 (Ser240/244) (Cell Signaling #9468) and p4EBP1 (Thr 37/46) (Cell Signaling #5123). Nuclei were visualized with Hoechst (ThermoFisher Scientific #H3570) staining. Cells were imaged (InCell 600) using respective fluorescence channels and the potency of mTOR inhibitors was defined by pS6 $IC_{50}$ (nM).

Generation of FKPB12 knock-out 293T cells. A CRISPR/Cas9 system was used to deliver ribonucleoprotein complexes containing guide RNA (gRNA) sequence that targets FKBP12 (GCCACTACTCACCGTCTCCT (SEQ ID NO: 1)) into 293T cells, using the Amaxa® 4D-Nucleofector™ X Kit (Lonza, V4XC-2032). Cell clones were screened by immunoblotting with an anti-FKBP12 antibody (Novus, NB300-508) and single clones demonstrating a complete FKBP12 knock-out (no measureable FKBP12) were selected.

Treatment of wild-type (WT) and FKBP12 knock-out 293T cells with RAD001 and Compound 1. WT and FKBP12 knock-out 293T cells were plated at a density of 30,000 cells per well in poly-D-Lysine coated 96-well plates (Corning, #354461) in Dulbecco's modified Eagle's medium (ThermoFisher, #11995-065) supplemented with 10% fetal bovine serum (ThermoFisher, #16140-071). Cells were incubated at 37° C., 5% $CO_2$ for 48 hours until they reached ~80% confluence. Cells were treated with RAD001 and Compound 1 using a 12-point dose range from 1000 nM to 0.0033 nM for 2 hours at 37° C. in duplicates. Media supplemented with blank Dimethyl sulfoxide (DMSO) was used as a control for both compounds. Phosphorylated amounts of S6K1 (Thr389) were detected by a sandwich ELISA kit (Cell signaling, #7063C) following the manufacture's protocol.

SPR assay to determine binding affinity to FK506-binding proteins (FKBP). N-terminal avi-his6 tagged FKBP fusions ("his6" disclosed as SEQ ID NO: 2) to FKBP12, FKBP51 and FKBP52 were expressed in *E. coli* and purified using standard chromatography. Each protein was subsequently immobilized on a streptavidin chip in a Biacore 8K SPR instrument (GE Healthcare). Using single-cycle kinetics, compound titrations were flowed at 45 uL/min over each surface using 2-minute association and 30-minute dissociation phases in a buffer containing 50 mM Tris pH 7.5/150 mM NaCl/0.01% Tween 20/1 mM DTT/2% DMSO. The data were fit using low molecular weight (LMW) single-cycle kinetics. The equilibrium dissociation constants ($K_D$) are reported.

Differential pharmacology of rapalogs may be achieved in different cell or tissue types depending on 1) the relative abundance of FKBP homologs in these cells/tissues and 2) the specificity of rapalogs for binding to these different FKBP homologs (Mol. Cell Biol. (2013) 33:1357-1367).

Results

In vitro potency of mTOR inhibitors was defined by pS6 $IC_{50}$ (nM) in MEF TSC1−/− cells for the compounds of the disclosure (Table 1).

TABLE 1

| Compound | IC50 (nM) |
|---|---|
| Rapamycin | 0.050 |
| RAD001 | 0.050 |
| 1 | 1.36 |
| 2 | 22.5 |
| 3 | 8.3 |
| 4 | 3.4 |

IC50 values are calculated as the average from multiple assays.

The equilibrium dissociation constants ($K_D$) to FKBP12, FKBP51, and FKBP52 are listed in Table 2 for the compound of the disclosure.

TABLE 2

| Compound | FKBP12 $K_D$ nM | FKBP12.6 $K_D$ nM | FKBP25 $K_D$ nM | FKBP51 $K_D$ nM | FKBP52 $K_D$ nM |
|---|---|---|---|---|---|
| RAD001 | 288 (n = 7) | 12 (n = 1) | 25 (n = 1) | 396 (n = 7) | 676 (n = 7) |
| 1 | 6.4 (n = 6) | 56 (n = 1) | 28900 (n = 1) | 2038 (n = 5) | 3548 (n = 5) |
| 4 | 10.9 (n = 4) | | | 2580 (n = 2) | 2578 (n = 2) |

mTORC1 Inhibition by Compound 1 is Specifically Dependent on FKBP12, while Other FKBPs in Addition to FKBP12 May Poteintiate RAD001 Effect.

Figure 1B:
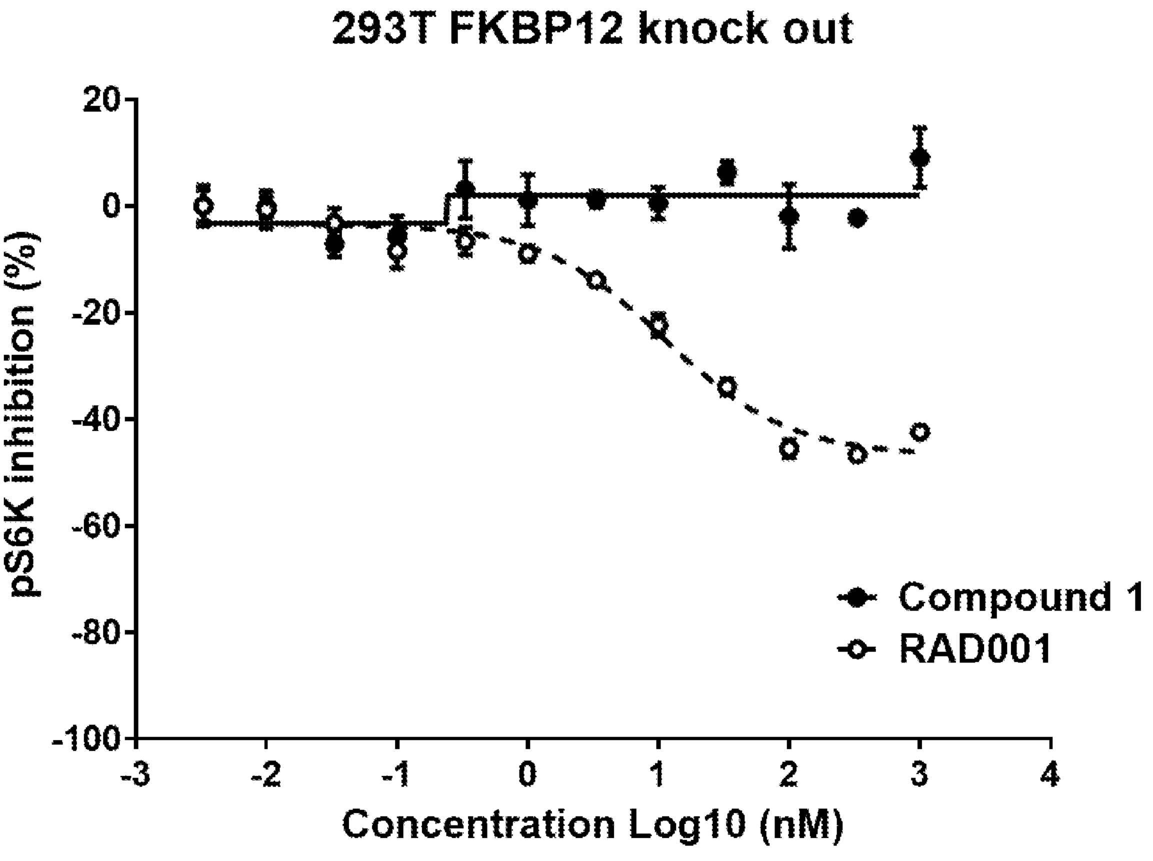

Phosphorylated amounts of S6K1 (Thr389) were measured in wild type and FKBP12 knock-out 293T cells, treated with Compound 1 or RAD001. S6K1 is a downstream target of mTORC1 and phosphorylation of its rapalog-sensitive Thr389 site is used as a functional readout of mTORC1 activity (Lee, C. H., Inoki, K. and Guan, K. L. (2007). mTOR pathway as a target in tissue hypertrophy. Annu. Rev. Pharmacol. Toxicol. 47, 443-467). In wild-type 293T cells, both Compound 1 and RAD001 were efficacious at achieving ~70-80% inhibition of S6K1(Thr389) phosphorylation (FIG. 1A). In the absence of FKBP12, Compound 1 no longer inhibited phosphorylation of S6K1(Thr389) at any tested concentration, while up to ~50% inhibition of S6K1(Thr389) was achieved with RAD001, demonstrating that RAD001 can act through other FKBPs besides FKBP1, whereas Compound 1 requires FKBP12 for its activity (FIG. 1B).

Without wishing to be bound by theory, these results indicate that the mTORC1 inhibitory effect of Compound 1 is mediated via FKBP12 alone; i.e. Compound 1 is highly selective for FKBP12, and therefore requires it for mTORC1 inhibition. On the contrary, in the case of RAD001, other FKBPs in addition to FKBP12 potentiate its ability to inhibit mTORC1. Based on the high specificity of Compound 1 for FKBP12, pharmacological effects of Compound 1 may be selective for cells where FKBP12 is the predominant homolog and where FKBP12 is expressed at sufficient levels, while avoiding mTORC1 inhibition in cells with low (insufficient) FKBP12 expression.

Having thus described several aspects of several embodiments, it is to be appreciated various alterations, modifications, and improvements will readily occur to those skilled in the art. Such alterations, modifications, and improvements are intended to be part of this disclosure, and are intended to be within the spirit and scope of the disclosure. Accordingly, the foregoing description and drawings are by way of example only.

We claim:

1. A compound of Formula (I) or a pharmaceutically acceptable salt thereof, wherein:

(I)

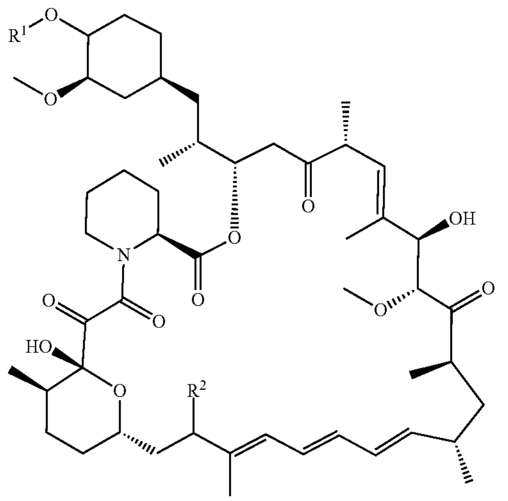

$R^1$ is selected from the group consisting of hydrogen, $C_{1-6}$ alkyl, hydroxyl$C_{1-6}$alkyl, and hetero$C_{1-6}$alkyl; and $R^2$ is

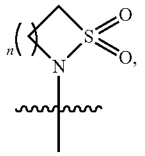

wherein n is 1, 2 or 3.

2. The compound of claim 1 or a pharmaceutically acceptable salt thereof, wherein $R^1$ is selected from the group consisting of hydrogen and

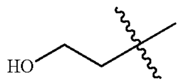

.

3. The compound of claim 1 or a pharmaceutically acceptable salt thereof, wherein $R_2$ is

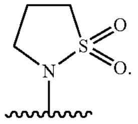

4. The compound of claim 1 or a pharmaceutically acceptable salt thereof, wherein $R_2$ is

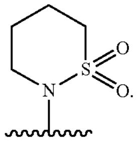 [SMILES: *N1CCCCS1(=O)=O]

5. A compound of structural formula:

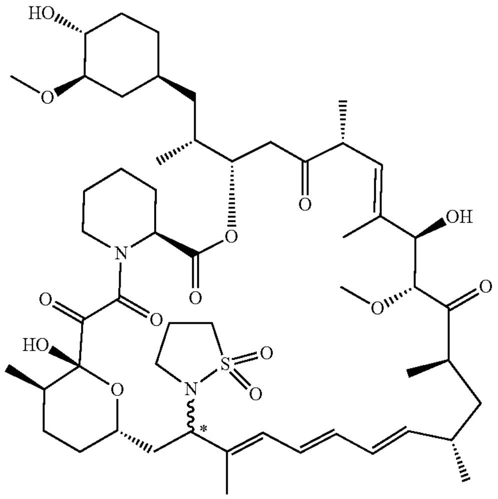 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(N3CCCS3(=O)=O)C[C@@H]3CC[C@@H](C)[C@@](O)(O3)C(=O)C(=O)N3CCCC[C@H]3C(=O)O2)CC[C@H]1O]

or a pharmaceutically acceptable salt thereof.

6. A compound of structural formula:

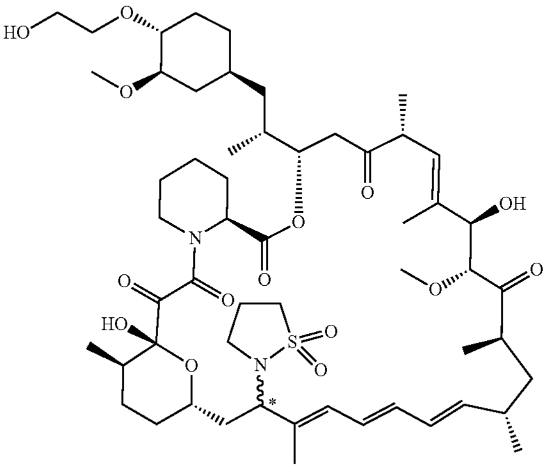 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(N3CCCS3(=O)=O)C[C@@H]3CC[C@@H](C)[C@@](O)(O3)C(=O)C(=O)N3CCCC[C@H]3C(=O)O2)CC[C@H]1OCCO]

or a pharmaceutically acceptable salt thereof.

7. A compound of structural formula:

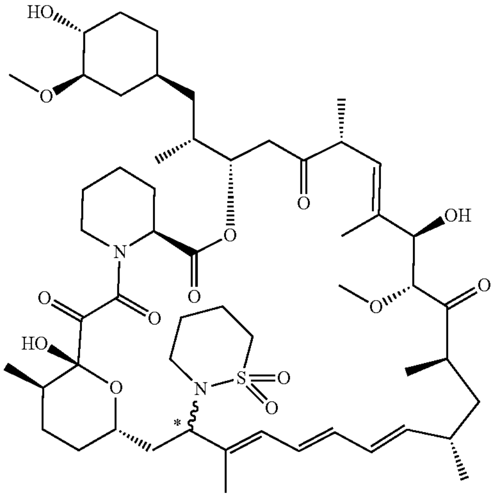 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(N3CCCCS3(=O)=O)C[C@@H]3CC[C@@H](C)[C@@](O)(O3)C(=O)C(=O)N3CCCC[C@H]3C(=O)O2)CC[C@H]1O]

or a pharmaceutically acceptable salt thereof.

8. A pharmaceutical composition comprising a therapeutically effective amount of a compound of claim 1 or a pharmaceutically acceptable salt thereof, and one or more pharmaceutically acceptable carriers.

9. A pharmaceutical combination comprising a therapeutically effective amount of a compound of claim 1 or a pharmaceutically acceptable salt thereof, and one or more therapeutically active agents.

10. A method for ameliorating or alleviating a disorder or a disease mediated by the mTORC1 pathway in a subject in need thereof, the method comprising administering to the subject a therapeutically effective amount of a compound of claim 1 or a pharmaceutically acceptable salt thereof.

11. The method of claim 10, wherein the disease or disorder is selected from sarcopenia, skin atrophy, cherry angiomas, seborrheic keratoses, brain atrophy, atherosclerosis, arteriosclerosis, pulmonary emphysema, osteoporosis, osteoarthritis, high blood pressure, cataracts, macular degeneration, glaucoma, stroke, cerebrovascular disease, chronic kidney disease, diabetes-associated kidney disease, impaired hepatic function, liver fibrosis, autoimmune hepatitis, endometrial hyperplasia, metabolic dysfunction, renovascular disease, hearing loss, mobility disability, cognitive decline, tendon stiffness, heart dysfunction, immune senescence, Parkinson's disease, Alzheimer's disease, cancer, immune-senescence leading to cancer due to a decrease in immune-surveillance, infections due to an decline in immune-function, chronic obstructive pulmonary disease, obesity, loss of taste, loss of olfaction, arthritis, and type II diabetes.

12. The method of claim 11, wherein the disorder is liver fibrosis.

13. A method of ameliorating or alleviating a disease or disorder mediated by the mTORC1 pathway in a subject in need thereof, the method comprising administering to the subject a therapeutically effective amount of a compound of claim 1 or a pharmaceutically acceptable salt thereof, wherein the disorder or disease is selected from:

Transplant vasculopathies;

Smooth muscle cell proliferation and migration leading to vessel intimal thickening, blood vessel obstruction, obstructive coronary atherosclerosis, restenosis;

Asthma;

Multi-drug resistance;

Age-related diseases;

Neurodegenerative diseases;

Seizures and seizure related disorders; and

Mitochondrial myopathy and mitochondrial stress.

14. The method of claim 10, wherein the disorder is a disorder that includes the process of fibrosis and/or inflammation.

15. The method of claim 10, wherein the disorder is selected from liver and kidney disorders.

16. The method of claim 15, wherein the liver disorder is selected from: liver fibrosis, which occurs in end-stage liver disease; liver cirrhosis; liver failure due to toxicity; non-alcohol-associated hepatic steatosis or NASH; and alcohol-associated steatosis.

17. The method of claim 15, wherein the kidney disorder is kidney fibrosis.

18. The method of claim 17, wherein the kidney fibrosis occurs as a result of acute kidney injury.

19. The method of claim 15, wherein the kidney disorder is chronic kidney disease.

20. The method of claim 15, wherein the kidney disorder is diabetic nephropathy.

21. A method of ameliorating or alleviating an age-related disorder or disease mediated by the mTORC1 pathway in a subject in need thereof, the method comprising administering to the subject a therapeutically effective amount of a compound of claim 1 or a pharmaceutically acceptable salt thereof, wherein the disorder or disease is selected from: sarcopenia, skin atrophy, cherry angiomas, seborrheic keratoses, brain atrophy, atherosclerosis, arteriosclerosis, pulmonary emphysema, osteoporosis, osteoarthritis, high blood pressure, cataracts, macular degeneration, glaucoma, stroke, cerebrovascular disease, chronic kidney disease, diabetes-associated kidney disease, impaired hepatic function, liver fibrosis, autoimmune hepatitis, endometrial hyperplasia, metabolic dysfunction, renovascular disease, hearing loss, mobility disability, cognitive decline, tendon stiffness, heart dysfunction, immune senescence, Parkinson's disease, Alzheimer's disease, cancer, immune-senescence leading to cancer due to a decrease in immune-surveillance, infections due to an decline in immune-function, chronic obstructive pulmonary disease, obesity, loss of taste, loss of olfaction, arthritis, and type II diabetes.

22. The method of claim 11, wherein the disease or disorder is selected from the group consisting of cardiac hypertrophy and/or systolic and/or diastolic dysfunction and/or hypertension and/or dilated cardiomyopathy, and heart dysfunction which results in a decline in ejection fraction.

23. The method of claim 11, wherein the disease or disorder is a complication stemming from type II diabetes, wherein the complication is selected from the group consisting of kidney failure, blindness, and neuropathy.

24. The method of claim 21, wherein the disease or disorder is selected from the group consisting of cardiac hypertrophy and/or systolic and/or diastolic dysfunction and/or hypertension and/or dilated cardiomyopathy, and heart dysfunction which results in a decline in ejection fraction.

* * * * *

```
                          SEQUENCE LISTING


<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1

gccactactc accgtctcct                                              20


<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 2

His His His His His His
1               5
```